(12) United States Patent
Marnay et al.

(10) Patent No.: US 7,491,204 B2
(45) Date of Patent: Feb. 17, 2009

(54) INSTRUMENTS AND METHOD FOR PREPARING AN INTERVERTEBRAL SPACE FOR RECEIVING AN ARTIFICIAL DISC IMPLANT

(75) Inventors: Theirry Marnay, Castelnau le Lez (FR); Rudolf Bertagnoli, Vienna (AT); Frank Magee, New York, NY (US); Stephan Eckhof, Tuttlingen (DE); David L. Nichols, New York, NY (US); Christophe Geisert, Tuttlingen (DE)

(73) Assignee: Spine Solutions, Inc., West Chester, PA (US)

( * ) Notice: Subject to any disclaimer, the term of this patent is extended or adjusted under 35 U.S.C. 154(b) by 648 days.

(21) Appl. No.: 10/423,879

(22) Filed: Apr. 28, 2003

(65) Prior Publication Data

US 2004/0215198 A1 Oct. 28, 2004

(51) Int. Cl.
*A61B 5/00* (2006.01)
(52) U.S. Cl. .................................................. 606/86 R
(58) Field of Classification Search .................. 606/53, 606/86, 99, 60, 61; 623/17.11–17.16
See application file for complete search history.

(56) References Cited

U.S. PATENT DOCUMENTS

| | | | |
|---|---|---|---|
| 4,697,586 A | 10/1987 | Gazale | |
| 4,878,915 A * | 11/1989 | Brantigan | 623/17.11 |
| 5,314,477 A | 5/1994 | Marnay | |
| 5,522,899 A * | 6/1996 | Michelson | 606/61 |
| 5,554,191 A * | 9/1996 | Lahille et al. | 623/17.11 |
| 5,571,109 A | 11/1996 | Bertagnoli | |
| 5,716,415 A | 2/1998 | Steffee | |
| 5,885,299 A * | 3/1999 | Winslow et al. | 606/99 |
| 6,042,582 A | 3/2000 | Ray | |
| 6,080,155 A * | 6/2000 | Michelson | 606/61 |
| 6,309,421 B1 | 10/2001 | Pisharodi | |
| 6,436,098 B1 | 8/2002 | Michelson | |
| 6,478,800 B1 | 11/2002 | Fraser et al. | |
| 6,517,544 B1 | 2/2003 | Michelson | |
| 6,524,318 B1 | 2/2003 | Longhini et al. | |
| 2001/0010002 A1 | 7/2001 | Michelson | |
| 2002/0016633 A1 | 2/2002 | Lin et al. | |
| 2002/0099377 A1 | 7/2002 | Zucherman et al. | |
| 2002/0111679 A1 | 8/2002 | Zucherman et al. | |
| 2002/0120259 A1 | 8/2002 | Lettice et al. | |
| 2002/0165612 A1 | 11/2002 | Gerber et al. | |

(Continued)

FOREIGN PATENT DOCUMENTS

FR 2 718 635 10/1995

(Continued)

*Primary Examiner*—Anu Ramana
(74) *Attorney, Agent, or Firm*—Stites & Harbison PLLC; Marvin Petry

(57) ABSTRACT

Instruments and methods for preparing an intervertebral space for receiving an implant. An adjustable trial implant has an adjustable stop mechanism having a stop member connected thereto to vary the distance that a body portion of the trial implant can move into the intervertebral space. Cutting tools for forming cutouts in the adjacent vertebrae use the trial implant and/or a guide to position a cutting tool which may be a burr or a chisel. The chisel cutting tool can be moveable relative to a selected trial implant or the chisel cutting tools can be fixed onto a trial implant shaped body portion.

39 Claims, 21 Drawing Sheets

U.S. PATENT DOCUMENTS

| | | |
|---|---|---|
| 2003/0045884 A1 | 3/2003 | Robie et al. |
| 2003/0055434 A1 | 3/2003 | O'Neil |

FOREIGN PATENT DOCUMENTS

| | | |
|---|---|---|
| FR | 2 737 656 | 2/1997 |
| WO | WO-01/01893 | 1/2001 |
| WO | WO-01/19295 | 3/2001 |

* cited by examiner

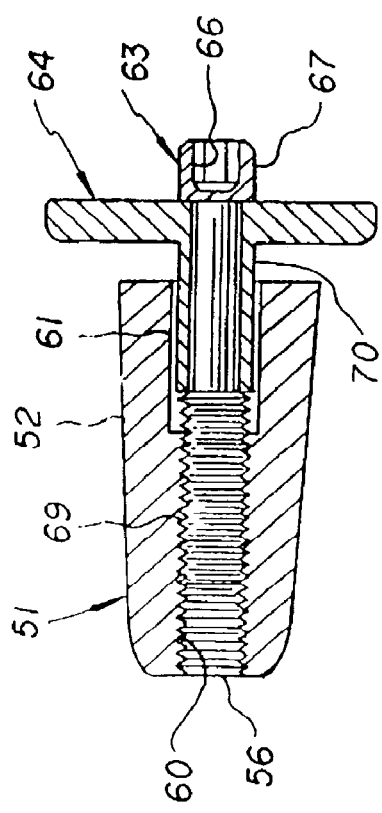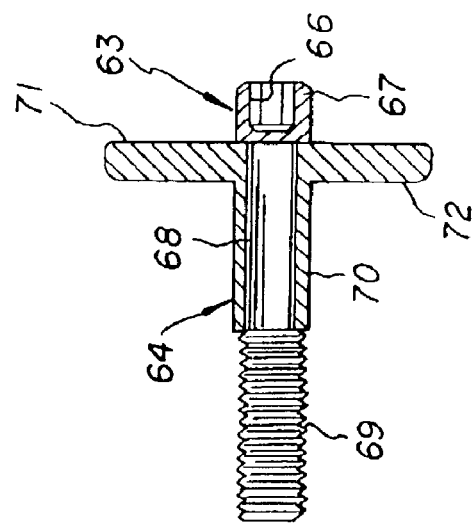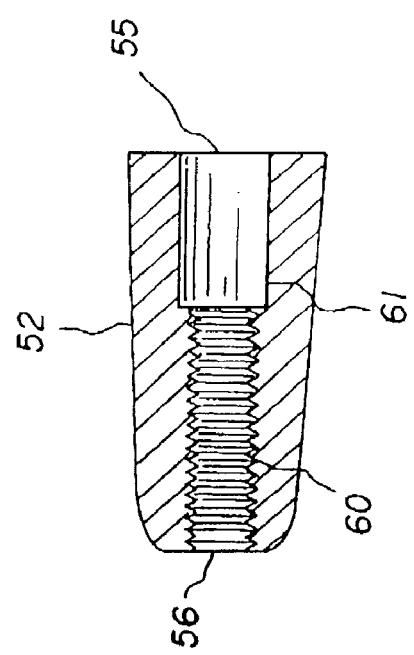

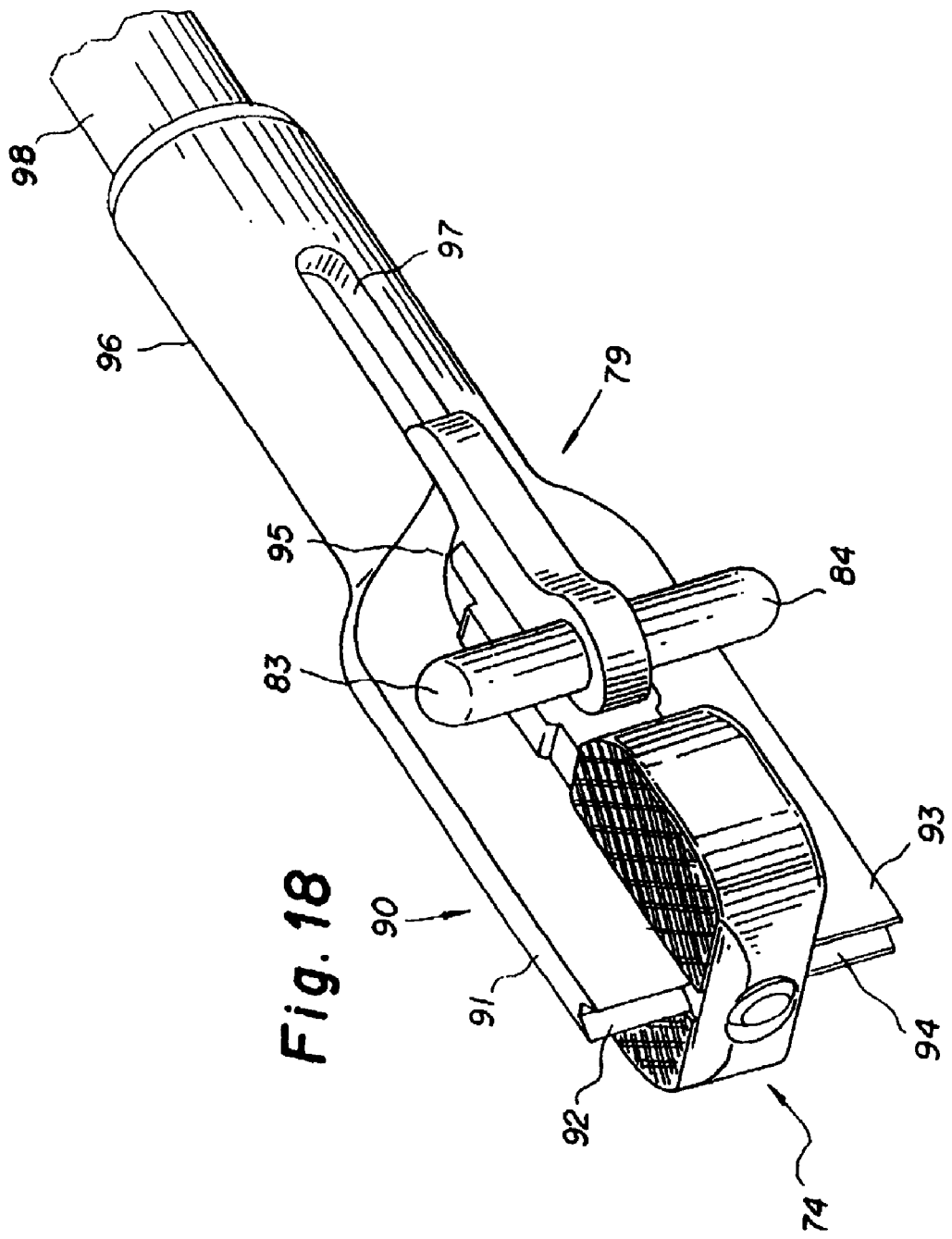

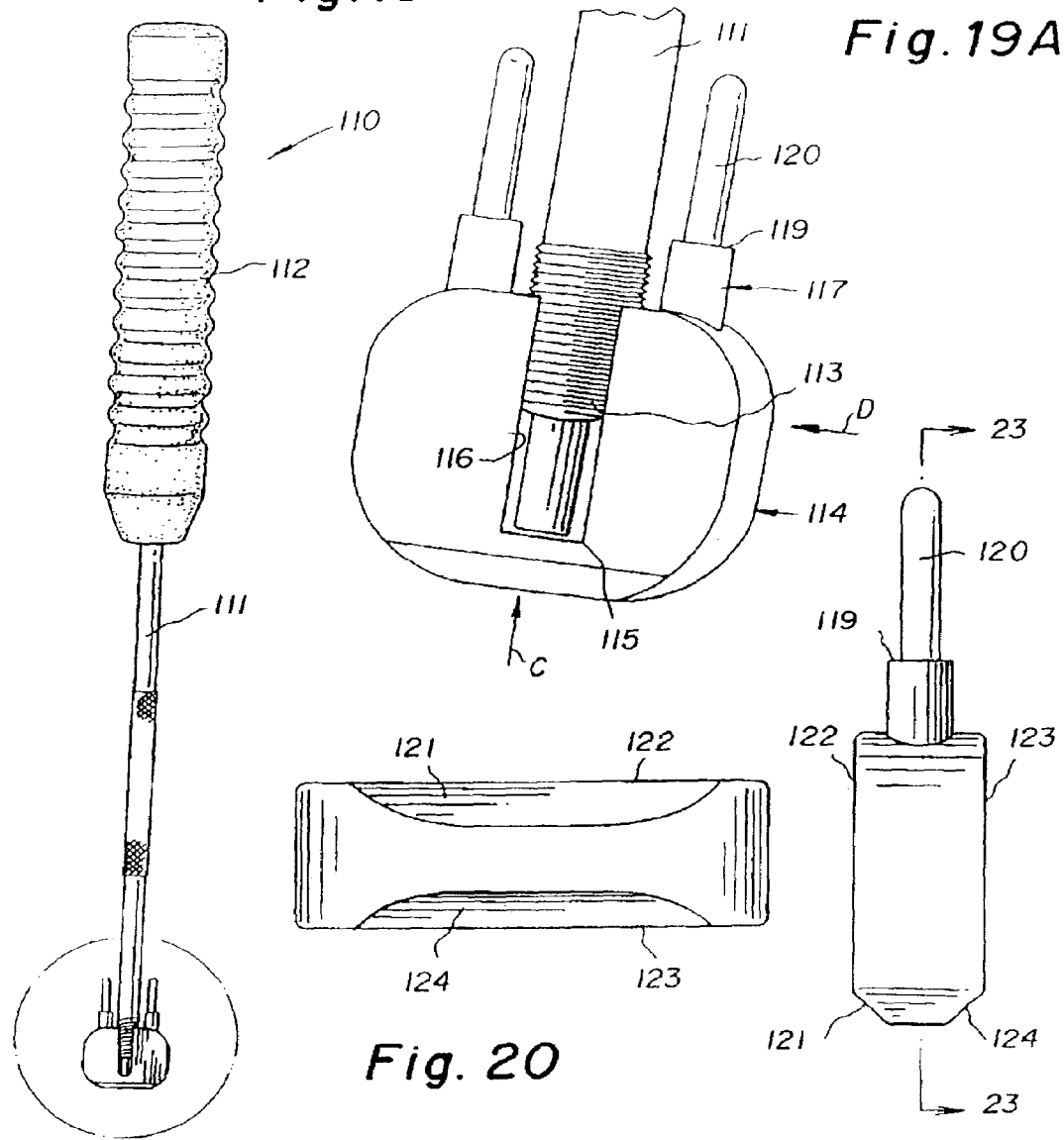

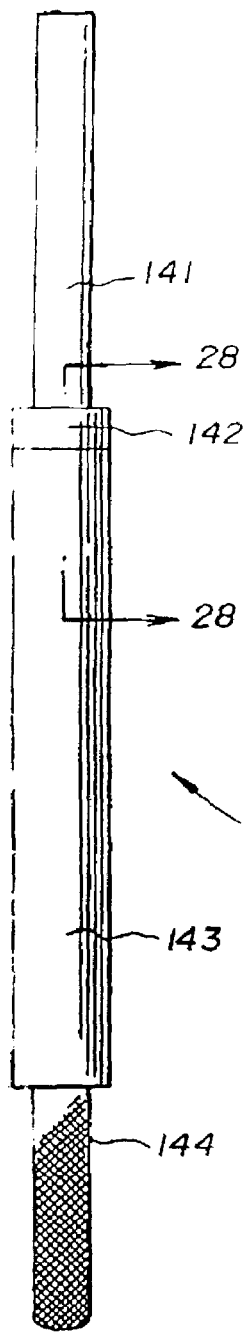
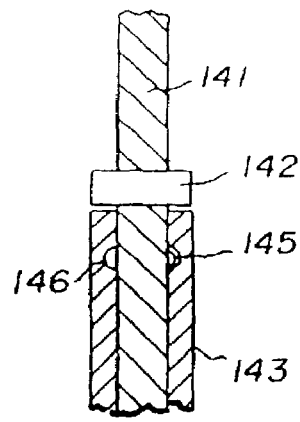
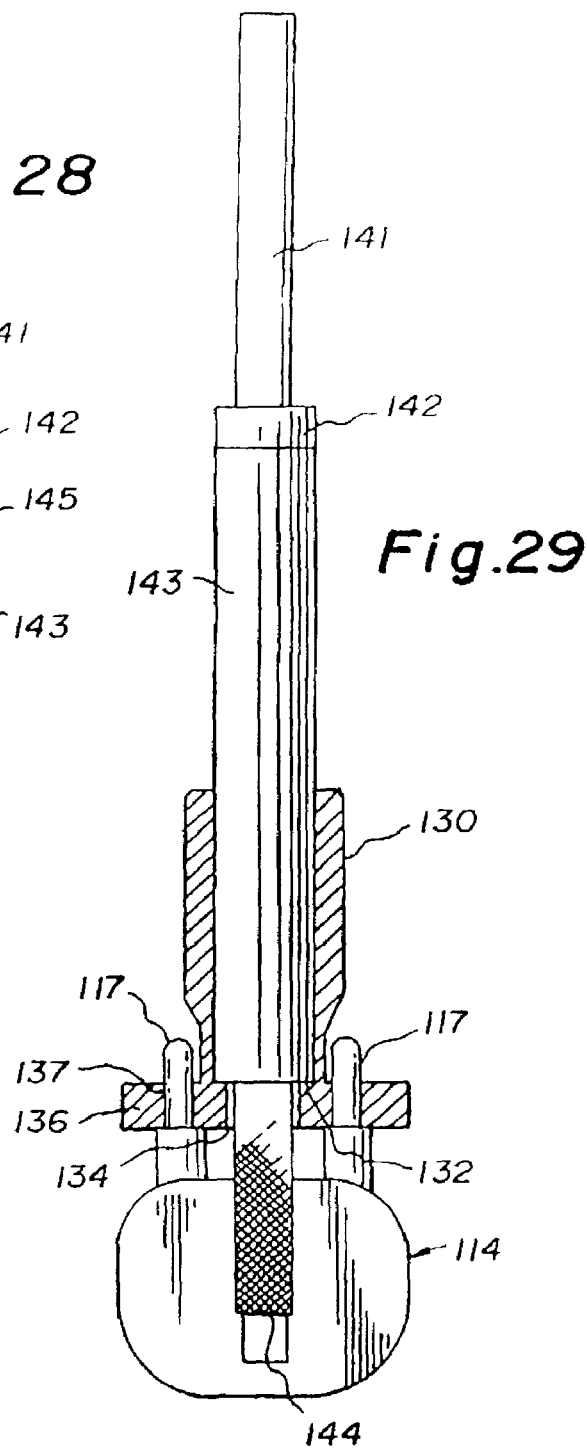
Fig. 27
Fig. 28
Fig. 29

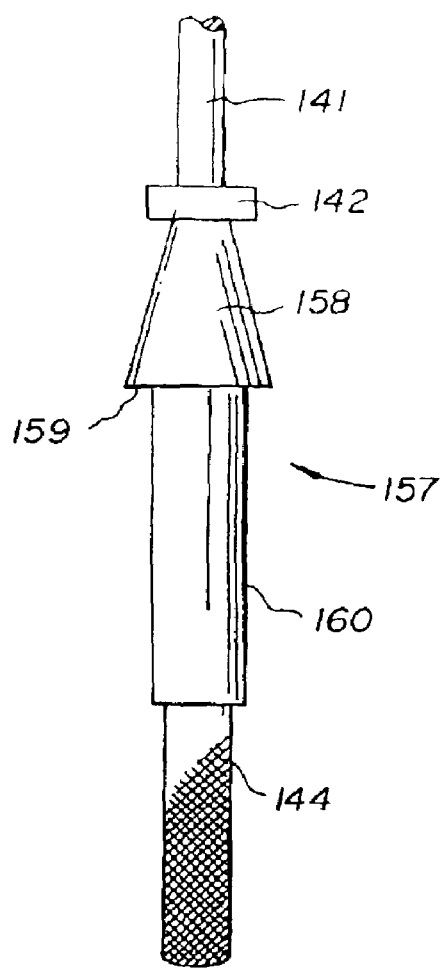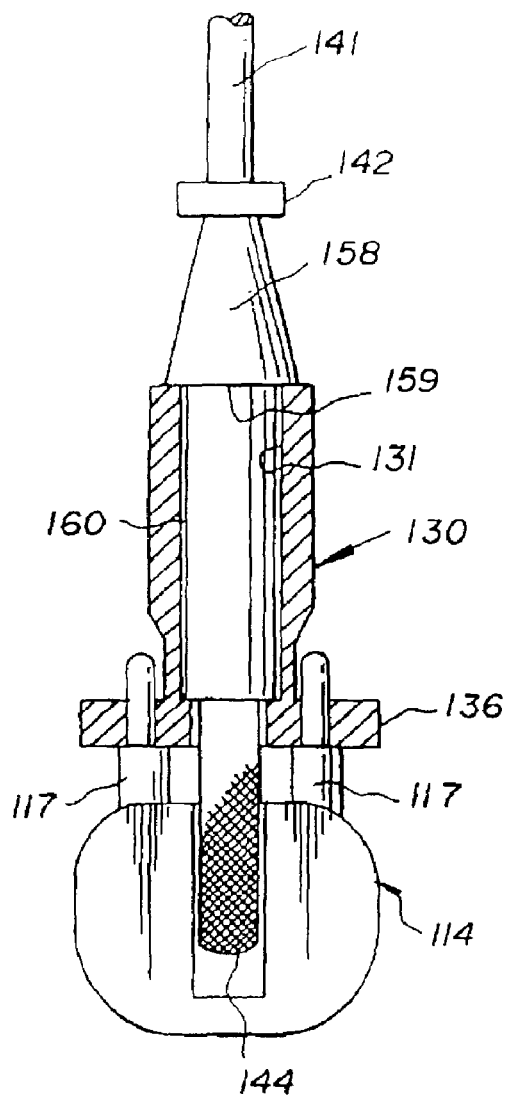

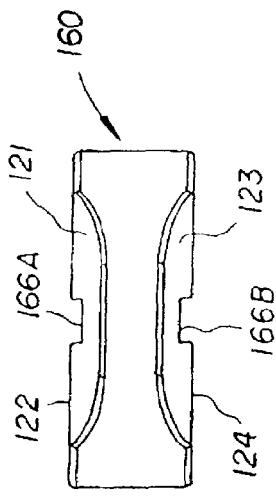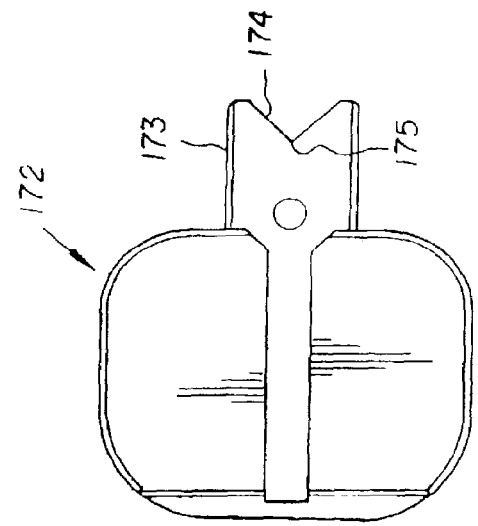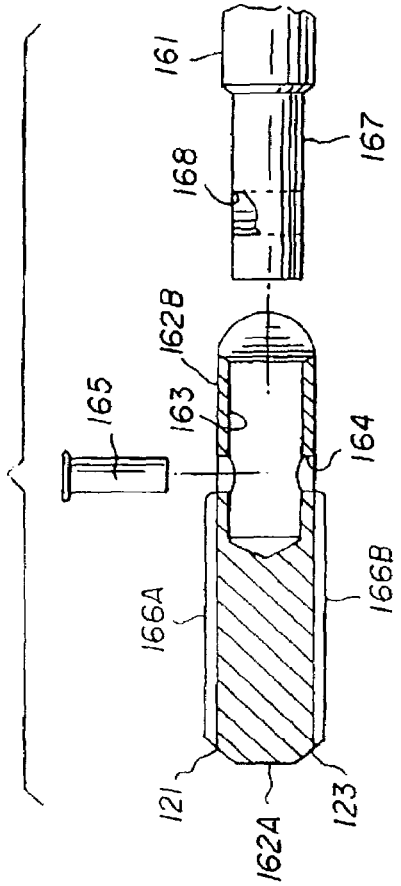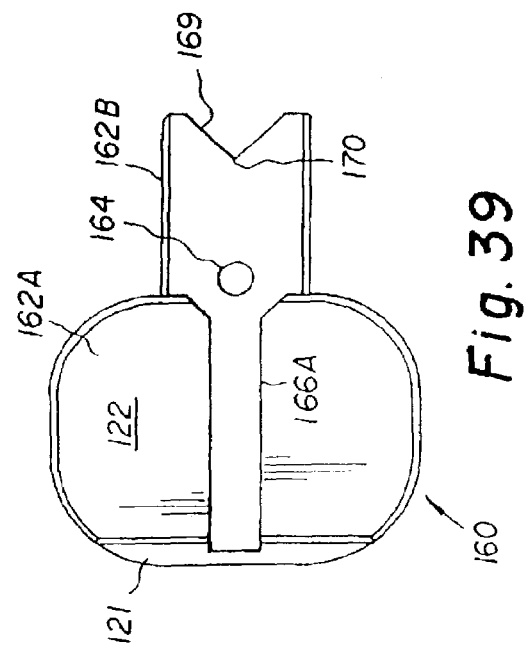
Fig. 37
Fig. 38
Fig. 39
Fig. 40

INSTRUMENTS AND METHOD FOR PREPARING AN INTERVERTEBRAL SPACE FOR RECEIVING AN ARTIFICIAL DISC IMPLANT

FIELD OF THE INVENTION

This invention relates to intervertebral implants, and more specifically, it relates to new and improved instruments and methods for preparing an intervertebral space for receiving an artificial intervertebral disc implant (sometimes referred to below simply as an implant).

BACKGROUND OF THE INVENTION

Currently, when it is necessary to completely remove a disc from between adjacent vertebrae, the conventional procedure is to fuse the adjacent vertebrae together. More recently, there have been important developments in the field of disc replacement, namely disc arthroplasty, which involves the insertion of an artificial intervertebral disc implant into the intervertebral space between adjacent vertebrae, and which allows limited universal movement of the adjacent vertebrae with respect to each other.

Some instruments have been developed to date for preparing an intervertebral space for receiving an artificial disc implant. These include a set of different sizes of trial implants, different ones of which are inserted into a cleaned out intervertebral space until the correct size trial implant has been determined, thereby determining the size of the actual implant to be inserted. The trial implant may have a fixed stop member in the form of a pin fixed to the rear end of the trial implant and extending vertically up and down for limiting movement of the trial implant into the intervertebral space. Some implants have a raised keel which requires that a cutout be formed in the vertebrae adjacent the intervertebral space for receiving these raised keels. One known arrangement for forming these cutouts is with a chisel which can be mounted to move along slots in the top and bottom of the selected trial implant as the chisel cuts into the adjacent vertebrae to form the cutouts.

One known artificial disc implant is shown in Published Application No. WO 01/01893, published Jan. 11, 2001, and instruments for inserting same are shown in Published Application No. WO 01/19295, published Mar. 22, 2001.

While these known instruments and methods represent a substantial improvement in the art, there exists a continuing need for improvements in the field of instruments and methods for preparing an intervertebral space for receiving an artificial intervertebral disc implant.

BRIEF SUMMARY OF THE INVENTION

The purpose of the present invention is provide new and improved instruments and related methods for preparing an intervertebral space for receiving an artificial intervertebral disc implant.

The instruments of the present invention may be used to prepare the intervertebral space at any location along the spine including especially the lumbar and cervical spines. However, since the cervical vertebrae are so small relative to the lumbar vertebrae, i.e., about 20% of the area of the lumbar spine vertebrae, some instruments may be more suited than others for the cervical spine.

The intervertebral implant is normally inserted from the patient's anterior moving towards the patient's posterior. However, it is to be understood that the implant, the instruments and the method can also be designed and arranged to insert the implant laterally, i.e., from the side, in which case the keels will be oriented on the implant for such lateral movement and the cutouts in the adjacent vertebrae will be opened toward a lateral side to receive the keel. To avoid confusion with respect to the patient's anatomy, the invention will be described herein with respect to more simple terminology which relates to the instruments and methods themselves. For example, in describing the invention, the terms "front" or "forward" mean the part of the instrument which faces toward the vertebrae or is moving in the direction of movement toward the vertebrae, while the words "back", "rear" or "rearward" refer to the end of the instrument farthest from the vertebrae or moving away from the vertebrae. Also, in this application, the words "upper" or "lower" or "uppermost" or "lowermost" or any other words describing the orientation of the intervertebral implant or the instruments or methods associated therewith are used only for convenience and are not intended to convey any limitation. More specifically, the parts of the implant, the instruments and/or the methods described in this application with reference to the upper part can in fact be positioned as the superior or inferior part within the patient's vertebrae, with the other of the two parts being the opposite part.

It is thus an object of the present invention to provide new and improved instruments for preparing an intervertebral space for receiving an artificial intervertebral disc implant.

The instruments and the methods of the present invention are particularly adapted for use with an artificial intervertebral disc implant having upper and lower parts which undergo limited universal movement with respect to each other, with the upper and lower surfaces of the upper and lower parts engaging the adjacent vertebral surfaces. Most of the instruments and methods of the present invention are also for use where the implant has a keel extending from the vertebrae engaging surfaces into cutouts formed in the adjacent vertebrae.

In accordance with a first aspect of the present invention, there is provided improved instruments and methods for inserting different size trial implants (until the correct trial implant has been determined) in combination with forming the cutouts in the vertebrae.

In accordance with a first embodiment of the present invention, any device moveable into an intervertebral space, for any purpose, can benefit by having associated therewith an adjustable stop mechanism which can allow that device to move variable distances into the intervertebral space. One example of a device which can benefit from having an adjustable stop mechanism is a trial implant. To properly test each trial implant, the trial implant must be moved to the center of the intervertebral space. However, in some patients, a bone spur or other irregularity may be engaged by a fixed stop member and therefore prevent the trial implant from moving further to its correct position in the intervertebral space. With an adjustable stop mechanism, if the trial implant reaches a limit position as permitted by an adjustable stop mechanism with a minimal insertion setting, which position does not position the trial implant correctly in the intervertebral space, the operator can then move back the adjustable stop to allow further movement of the trial implant to its correct position within the intervertebral space.

In accordance with another embodiment of the invention, after the correct size trial implant has been determined, the selected trial implant is placed within the intervertebral space and a guide is slid down over the shaft of the trial implant insertion tool until the guide engages the trial implant. Thereafter, the trial implant insertion tool shaft is removed and a cutting tool is passed through the guide and into a slot within the trial implant. If the cutting tool is a burr, the burr, including a spacer sleeve determines the exact positioning of the burr in the guide, and hence the depth of the burr itself into the trial implant and thus subsequently into the adjacent vertebrae.

Power means are then provided to rotate the burr and move it from end to end within the guide to form the cutouts in the adjacent vertebrae. The end limits of a slot in the guide will determine the outer limits of movement of the burr, and hence the upper and lower limits of the cutouts.

In accordance with another embodiment of the present invention, after the correct trial implant has been selected, that selected trial implant can be used in combination with a chisel for cutting the vertebrae to form the cutouts. A chisel can be used instead of a burr with the guide discussed above. The chisel arms would pass through and be guided by the elongated slot opening.

In accordance with another arrangement which uses a chisel, the trial implants have a body portion and a tail section. A holding device is connected to the tail section. The holding device may comprise a shaft. These trial implants have front to rear slots formed in the top and bottom thereof. After the correct trial implant has been selected, a chisel with upper and/or lower arms and a hollow shaft is slid along the trial implant insertion tool shaft until the upper and/or lower arms of the chisel ride over the selected trial implants, through the slots formed in the top and bottom thereof. Trial implants with larger surface areas would have smaller tail sections so that the same chisel can be used for all trial implants of the same height but with differing surface areas.

In accordance with another embodiment of the present invention, the chisel cutting tools are formed integrally with a body portion which is the exact same shape and size of the body portion of the selected trial implant, so that instead of the chisel riding over a selected trial implant, the entire unit of a body portion the same size and shape as the body portion of the selected trial implant with a chisel cutting tool fixed thereto is moved into the intervertebral space as the chisel cutting tool cuts into the vertebrae to form the cutouts.

Thus, it is an object of the present invention to provide new and improved instruments for preparing an intervertebral space for receiving an artificial disc implant.

It is another object of the present invention to provide new and improved methods for preparing an intervertebral space for receiving an artificial disc implant.

These and other objects of the present invention will be apparent from the detailed description to follow, together with the accompanying drawings.

BRIEF DESCRIPTION OF THE DRAWINGS

Preferred embodiments of the invention will now be described by way of example with reference to the accompanying drawings, wherein:

FIG. 7 is a cross sectional view taken along line 7-7 of FIG. 6, referred to hereinafter as the plane of the adjustable stop mechanism;

FIG. 8 is a cross sectional view through an adjustable stop mechanism;

FIG. 9 illustrates the adjustable stop mechanism of FIG. 8 mounted in the trial implant of FIG. 7;

FIG. 18 is a perspective view similar to FIG. 12 but including a chisel cutting tool positioned thereon;

FIG. 19 is a perspective view illustrating an instrument for inserting trial implants;

FIG. 19A is an enlarged perspective view of the portion of FIG. 19 shown in the broken line circle;

FIG. 20 is an end view of the trial implant of FIG. 19, taken in the direction of the arrow C of FIG. 19A;

FIG. 21 is a side view of the trial implant of FIG. 19, taken in the direction of the arrow D of FIG. 19A;

FIG. 27 is a side elevational view of a burr;

FIG. 28 is a partial cross sectional view taken along line 28-28 of FIG. 27;

FIG. 29 is a cross sectional view showing the trial implant and the burr guide, together with the burr of FIG. 27;

FIG. 34 is a side elevational view of a modified burr;

FIG. 35 is a cross sectional view showing the burr of FIG. 34 and the burr guide of FIGS. 24 and 25;

FIG. 37 is a central cross sectional view of the trial implant shown in FIG. 36;

FIG. 38 is a left end view of FIG. 37;

FIG. 39 is a plan view of FIG. 37;

FIG. 40 is a plan view similar to FIG. 29 but showing a different size trial implant;

DETAILED DESCRIPTION OF THE PREFERRED EMBODIMENTS

Figure 1:
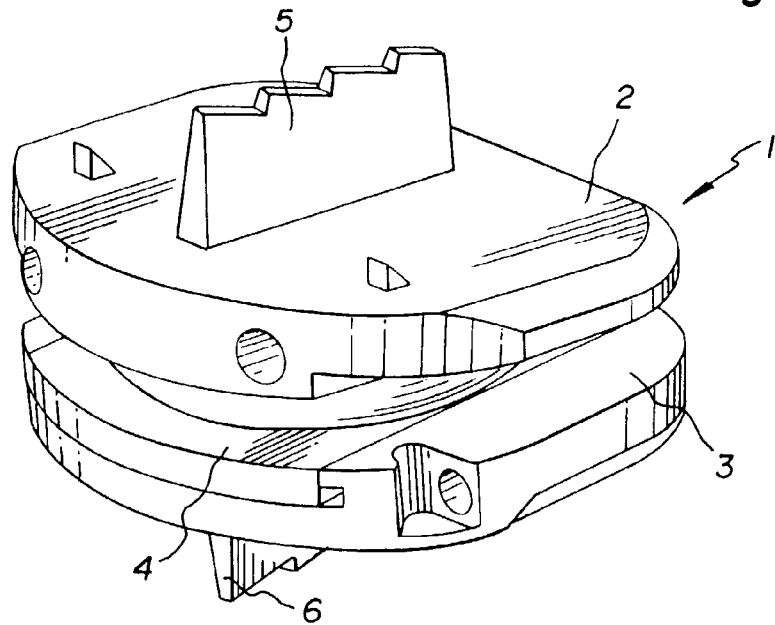
FIG. 1 is a perspective view of one type of intervertebral implant for which the instruments and method of the present invention are utilized to prepare the intervertebral space.

Referring now to the drawings, like elements are represented by like numerals throughout the several views.

The instruments and methods described herein are applicable for preparing a wide range of artificial disc implants for insertion into an intervertebral space. The instruments and method described herein which relate to the trial implant but which do not necessarily relate to cutting tools for forming cutouts can be used for virtually any type of artificial disc implant wherein an intervertebral space is cleaned out and an entire replacement implant is inserted into that intervertebral space. For those instruments and methods described herein which include the concept of forming cutouts to receive raised keels, the instruments and methods described herein are adaptable for use with any artificial disc implant having such keels.

A first type of artificial disc implant having raised keels is shown in FIG. 1. As shown therein, this artificial disc implant 1 has an upper plate 2 and a lower plate 3 which are spaced apart by a plastic inlay 4. The upper plate 2 has a raised keel 5 and the lower plate 3 has a raised keel 6. The artificial disc implant shown in FIG. 1 can be used at any location along the spine including the cervical spine or the lumbar spine, but this particular artificial disc implant might be particularly suitable for the lumbar spine. This particular artificial disc implant is shown and described in greater detail in Published Application No. WO 01/01893, published Jan. 11, 2001.

Figure 2:
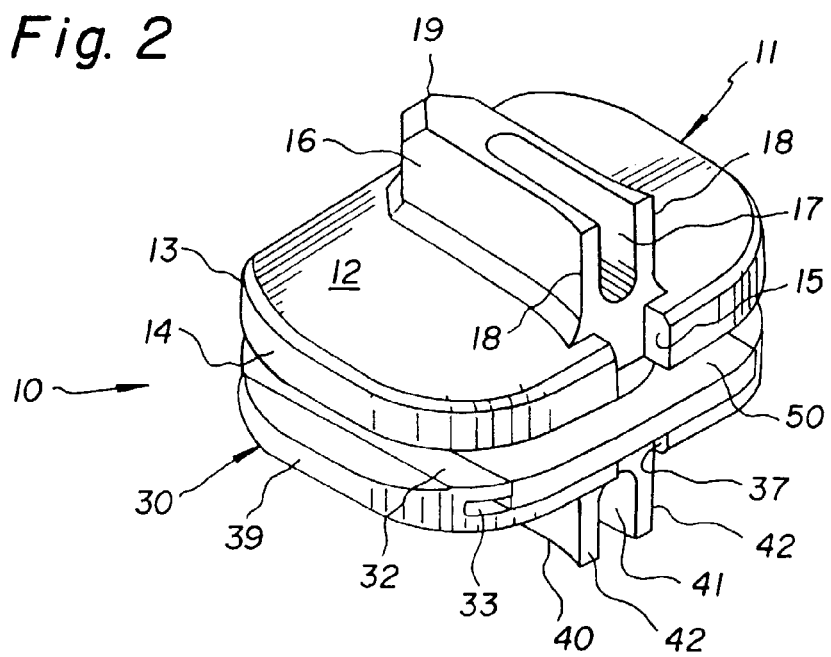
FIG. 2 is a perspective view of another type of intervertebral implant for which the instruments and method of the present invention are utilized to prepare the intervertebral space.

FIG. 2 illustrates another implant having raised keels which are intended to be located in cutouts in the adjacent vertebrae. Although the artificial disc implant of FIG. 2 can also be used for any location along the spine, including the cervical spine or the lumbar spine, this particular design has advantages for use in the cervical spine. The artificial disc implant 10 of FIG. 2 has an upper part 11 and a lower part 30 and a plastic inlay 50 located therebetween but essentially connected to the lower part 30. This plastic inlay has a curved surface which cooperates with a curved bottom surface of upper part 11 to allow limited universal movement of the upper and lower parts relative to each other.

The upper part 11 includes an upper surface 12, which engages and supports the adjacent vertebral surface. Upper surface 12 is bounded by edges which are slightly beveled all the way around as shown at 13 with the largest portion of the bevel being shown along the rear surface. Below the beveled edge 13, the upper part is bounded by a surrounding side wall 14 which has a rear support cutout 15.

Rising above the upper surface 12 of the upper part 11 is a keel 16 which includes a recess 17 formed therein. This recess is opened upwardly and rearwardly. The front end of keel 16 comprises a V-shaped upper bevel 19. The lower portion of the front end of the keel is in the form of a V-shaped bevel 20. The two V-shaped bevels 19 and 20 provide a front end which is "arrow" shaped in order to facilitate insertion of the keel into a cutout formed in the adjacent vertebrae. The rear opening of the recess is flared at 18 to anchor the rear end of the keel 16 in its cutout in the adjacent vertebrae.

The lower part 30 includes a rear support cutout 37. A keel 40 rises upwardly (or in the usual orientation, extends downwardly). This keel includes a recess 41 which opens downwardly and rearwardly and has a flared entrance at 42 which serves the same function as flared entrance 18, i.e., to facilitate engagement of the rear end of the keel within its cutout in the vertebrae. Recess 41 opens downwardly and rearwardly. At its front end, the keel 40 includes a V-shaped lower bevel like that of the upper part 11.

After an intervertebral space has been cleaned out in preparation for receiving an artificial disc implant, the next procedure is to determine the precise size of the artificial disc implant which is correct for that particular intervertebral space. This is accomplished by providing a set of trial implants of different sizes. For example, a set of trial implants may include trial implants of approximately three different surface areas, each provided for a plurality of heights, for example three to five different heights 1 mm apart. The operator would select the trial implant which from experience the operator believes would be the most appropriate trial implant for that particular intervertebral space. Generally the operator would start with a trial implant which, if not correct, would be on the small side. Working from that initial selection, if it did not turn out to be a perfect fit, the operator would try other trial implants of the set, generally going up in height and/or surface area, as the operator deems appropriate, until finally the correct size trial implant is determined.

The operator needs a mechanism for providing a physical "feel" to know when the trial implant has been inserted the proper distance into the intervertebral space. Known trial implants have a fixed stop member mounted on the rear of each trial implant, which stop member would engage the vertebrae to limit movement of the trial implant into the intervertebral space. If the vertebrae has an irregularity on the anterior side thereof, or is of an irregular shape, a fixed stop might engage that irregularity and stop the trial implant before it reaches the proper position within the intervertebral space. With the adjustable stop mechanism of the present invention, the operator, after "feeling" that the trial implant has gone as far as permitted by the current setting of the adjustable stop mechanism, and determining with instruments that the trial implant has not reached its proper position within the intervertebral space, would move the adjustable stop rearwardly to allow the trial implant to advance further into the intervertebral space.

FIGS. 3-11B illustrate a trial implant having an adjustable stop mechanism having a movable stop member. With the adjustable stop mechanism of the present invention, the stop member would first be placed at its position closest to the rear of the body portion of the trial implant, thus minimizing penetration of the trial implant into the intervertebral space. Then, with the assistance of radiographic monitoring, if it was observed that the trial implant was stopped prematurely, the adjustable stop mechanism would be manipulated to gradually move the stop member away from the rear of the trial implant, allowing the trial implant to move farther into the intervertebral space until the trial implant is properly positioned therein.

Figure 3:
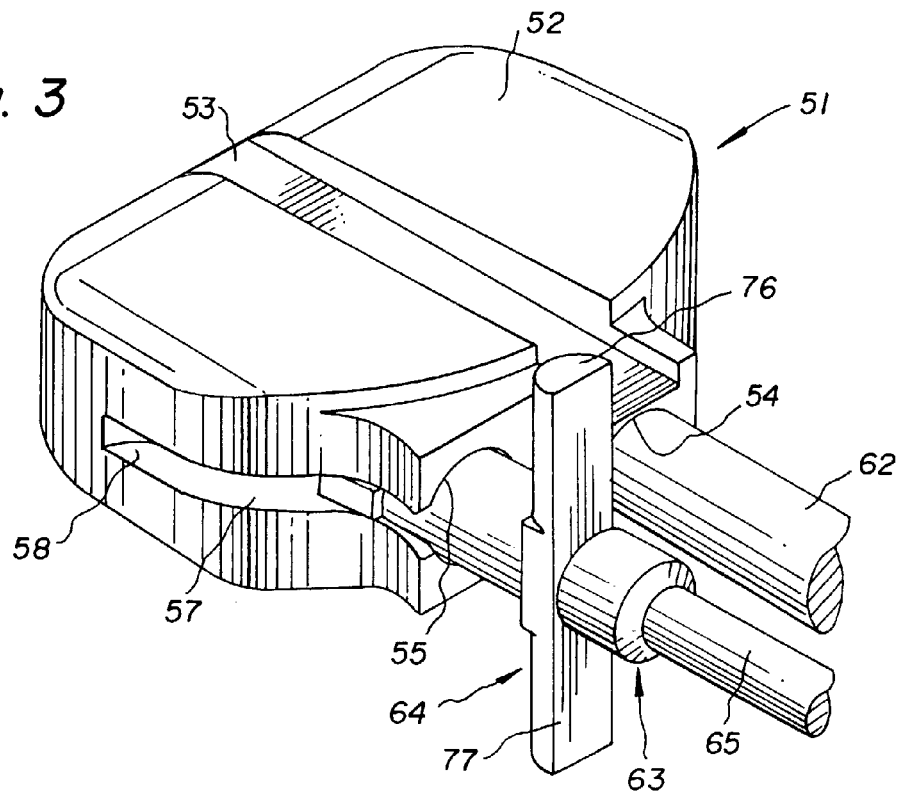
FIG. 3 is a perspective view a trial implant having an adjustable stop mechanism.
Figure 4:
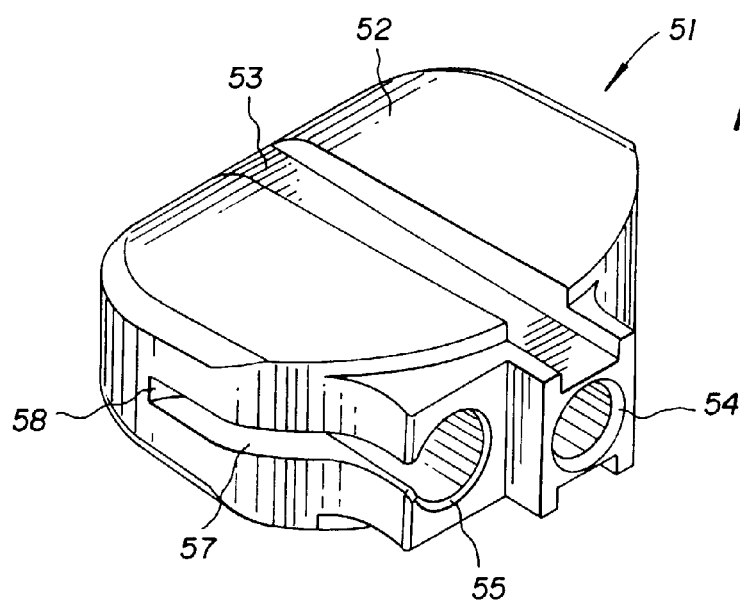
FIG. 4 is a rear perspective view of a trial implant adapted to receive an adjustable stop mechanism.
Figure 5:
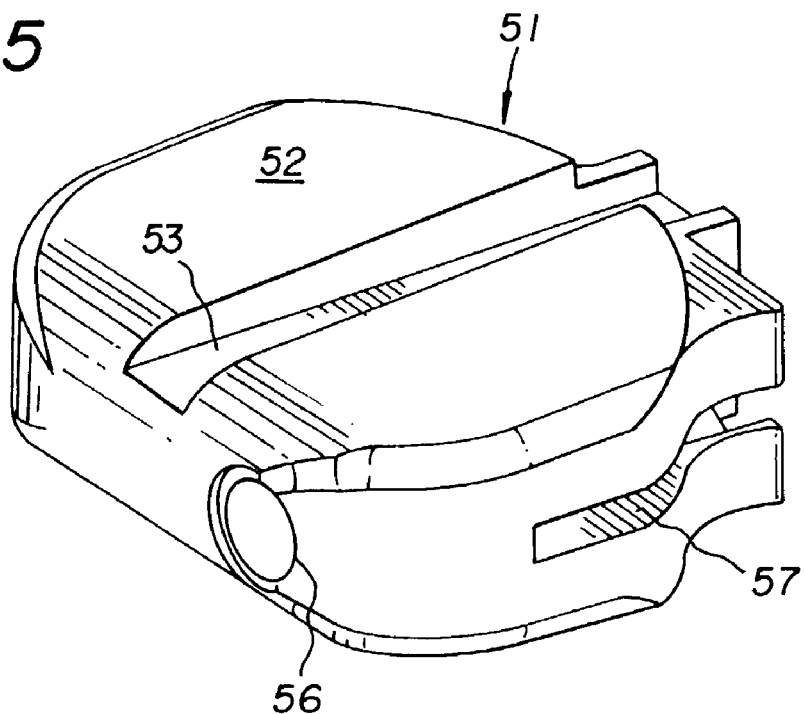
FIG. 5 is a front perspective view of a trial implant adapted to receive an adjustable stop mechanism.
Figure 6:
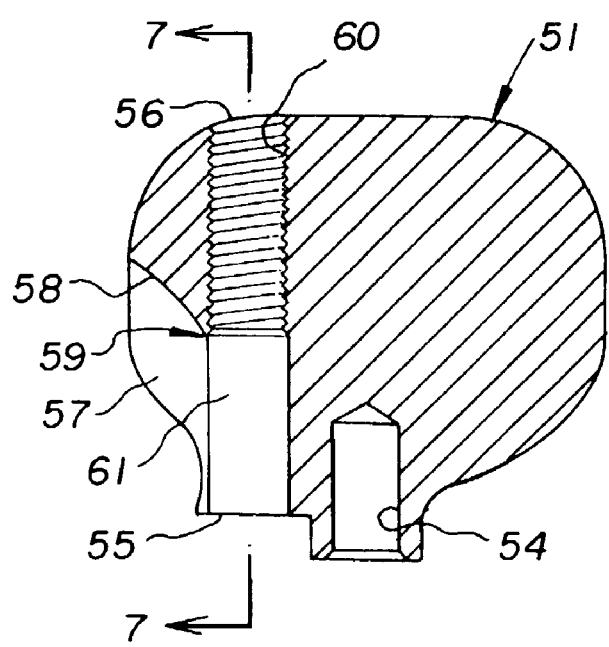
FIG. 6 is a horizontal sectional view taken centrally through the embodiment shown in FIGS. 4 and 5.

FIG. 3 is a perspective view of a trial implant having an adjustable stop mechanism. The trial implant 51 includes a body portion having a top and bottom 52. A pair of front to rear slots 53 may be provided in the top and bottom thereof if desired in order to cooperate with a chisel cutting tool and hence may be omitted if it is not desired or necessary to subsequently utilize a chisel cutting tool which slides along slots of a trial implant. It is to be understood that the trial implant 51 would be one of a plurality of trial implants of a set, as described above. The trial implant would be held by a holding device. In the illustrated embodiment, a rear opening 54 is provided for a holding device in the form of an elongated shaft 62 which would be grasped by the operator. The shaft 62 can be threaded into opening 54, thereby permitting a given shaft to be used with different trial implants, or if it is believed more convenient or economical, each trial implant can be provided with a shaft 62 fixed in the opening 54. Referring also to FIGS. 4-6, the trial implant has an elongated bore therethrough in the front to rear direction starting from a rear opening 55 to a front opening 56. The rear portion 61 of this bore is smooth, i.e., not threaded, whereas the front portion 60 of this bore is threaded. The unthreaded smooth portion 61 opens into a slotted cutout 57 which is defined above and below by parallel horizontal surfaces and at the forward end by a wall 58 which extends from the side periphery of the trial implant to an end point 59 at the juncture between the smooth portion 61 and the threaded portion 60 of the elongated bore. The bore itself is shown in vertical cross section in FIG. 7.

FIG. 8 illustrates the two parts of the adjustable stop mechanism, an adjustment member 63 and a stop member 64. The adjustment member 63 includes a cylindrical enlarged member 67 having a socket 66 therein for receiving a screwdriver or the like (see FIG. 3) for turning the cylindrical member 67 and hence also the entire adjustment member 63. To the left of cylindrical member 67, the adjustment member 63 includes a smooth shaft portion 68 of reduced cross section and to the left thereof threads 69 having an outer diameter greater than the diameter of the smooth shaft 68. Mounted on the adjustment member 63 is the stop member 64 which comprises a hollow sleeve portion 70 which rotates freely on the smooth shaft 68. The stop member 64 includes at least one pin but preferably two pins, namely upper and lower pins 71 and 72. It will be noted that the stop member 64, while freely rotatable on the shaft 68, is prevented from moving laterally along the adjustment member 63, limited to the left by the larger diameter threads 69 and limited to the right by engagement of the pins 71 and 72 with the left end of cylindrical member 67.

Figure 10:
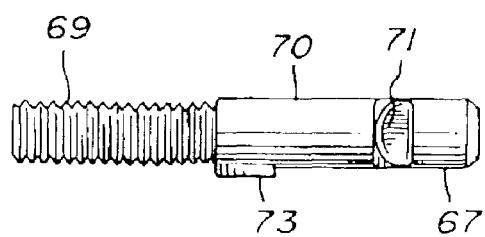
FIG. 10 is a plan view of the adjustable stop mechanism of FIG. 8.
Figure 11A:
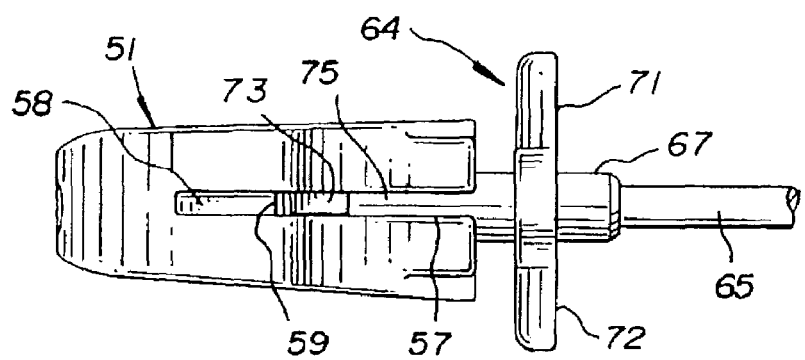
FIG. 11A is a side elevational view of a trial implant and an adjustable stop mechanism in a first position.
Figure 11B:
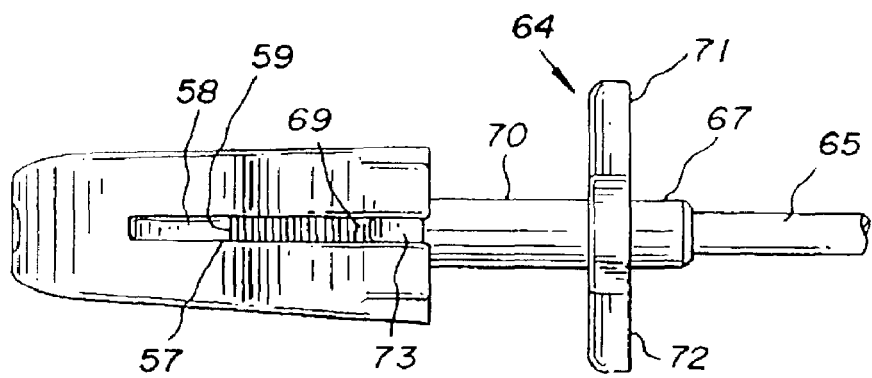
FIG. 11B is similar to FIG. 11A but shows the adjustable stop mechanism in a different position.

Referring to FIGS. 10, 11A and 11B, the sleeve 70 includes a raised rectangular lug 73. Referring to FIG. 9, it can been seen that if the assembly of the adjustment member and the stop member are inserted through the opening 55 and into the bore 61 until the threads 69 engage the threads 60, continued rotational movement of the adjustment member 63, by engaging the socket 66 with a screwdriver or the like, will cause the entire unit of the adjustment member and the stop member to advance towards and through the trial implant without necessarily rotating the stop member. In fact, as the front end of sleeve 70 enters the rear opening 55 of the trial implant, the square lug 73 is positioned to ride within the slot 57, thereby preventing rotational movement of the stop member 64 as the entire adjustable stop mechanism advances.

The operation of the adjustable stop mechanism will be more evident by referring to FIGS. 11A and 11B. Referring first to FIG. 11B, the operator would grasp the socket 66 with the screwdriver 65 and turn the adjustment member 63 when the threads 69 first engaged the threads 60, in the meantime manipulating the stop member 64 rotationally to ensure that the lug 73 entered the slot 57, thereby preventing rotational movement of the stop member 64. The operator would then advance the adjustment member and stop member as far as possible through the bores 60, 61 until the arms 71 and 72 were up against the back of the trial implant, at which time the lug 73 would be stopped by engagement with the end 59 of side wall 58. In this position, the body portion of the trial implant would be inserted into the patient's intervertebral space. With the assistance of radiographic monitoring, the operator would then determine whether the trial implant had moved to its proper position. If not, the operator would then turn the shaft 65 in precisely defined amounts (for example one full turn equaling 1 mm in depth in the disc space), thus allowing the body portion of the trial implant to progress into the intervertebral space. FIG. 11B might represent an end position wherein the adjustment member and stop member have been pulled out, and hence the body portion of the trial implant inserted into the intervertebral space to a desired position.

Figure 12:
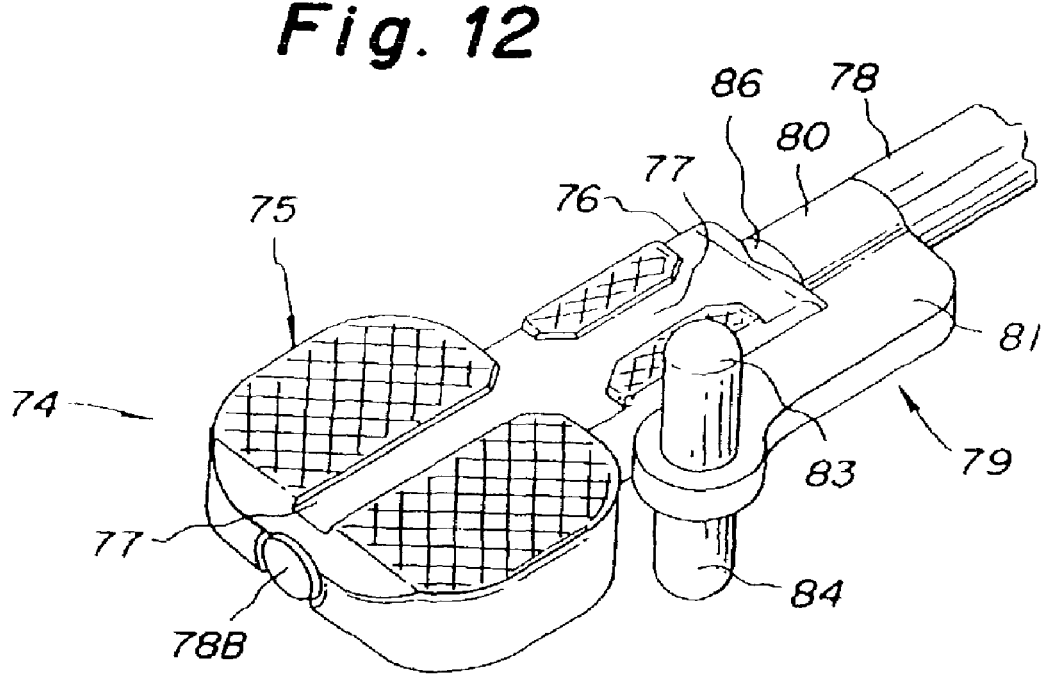
FIG. 12 is a perspective view of another embodiment of a trial implant having an adjustable stop mechanism.
Figure 13:
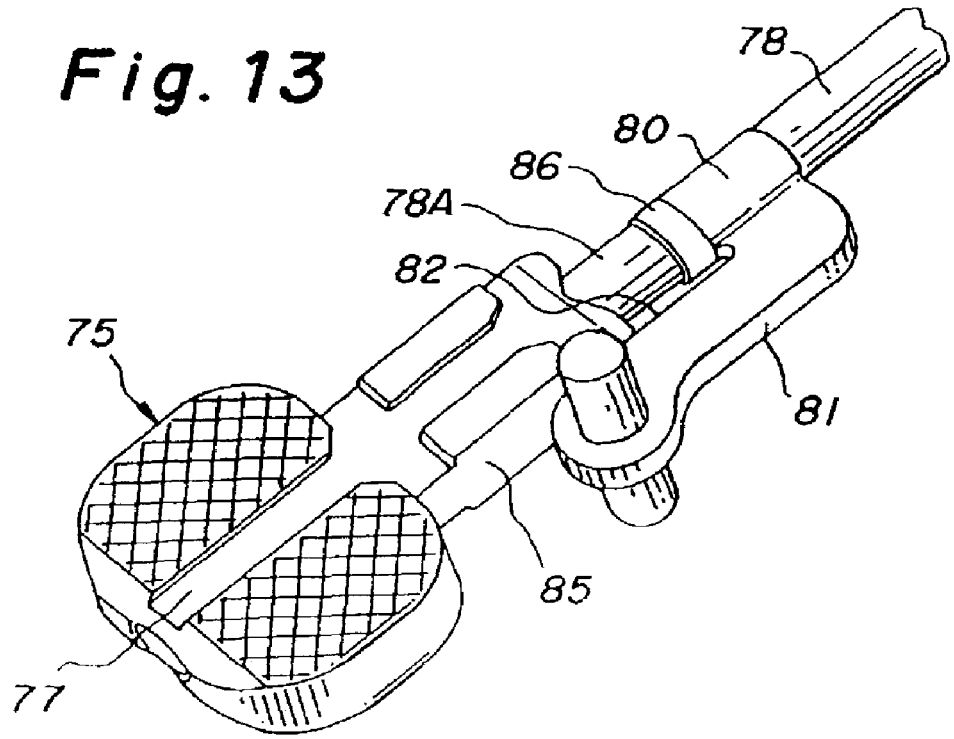
FIG. 13 is a perspective view similar to FIG. 12 but showing the parts in a moved position.
Figure 16:
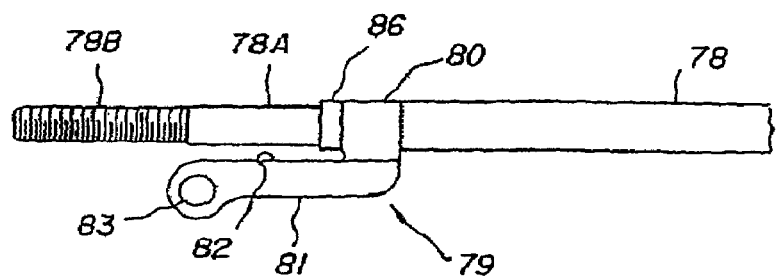
FIG. 16 is a plan view of an element of FIG. 12, removed from the trial implant.

FIGS. 12-18 illustrate another embodiment of a trial implant having an adjustable stop mechanism. FIGS. 12 and 13 are perspective views of this embodiment of a trial implant, each showing the adjustable stop mechanism in one of its two end positions. Referring to FIGS. 12-16, trial implant 74 includes a body portion 75 and a tail section 76. A slot 77 along the entire top and bottom of the trial implant receives a chisel cutting tool, as will be described below. Referring especially to FIG. 16, a shaft 78 which at its remote, right-hand end would have a handle attachable thereto, includes an unthreaded middle section 78A and a threaded forward section 78B.

The adjustable stop mechanism 79 comprises a sleeve 80 which is freely rotatable about the shaft middle section 78A adjacent the point where this section steps up in diameter to the main portion of shaft 78. Immediately forward of this freely rotatable sleeve 80, a washer 86 is fixed by welding or the like to the middle shaft section 78A. Accordingly, the sleeve 80 is mounted to rotate freely about the middle section 78A but is prevented from moving longitudinally along shaft 78 or middle section 78A.

The adjustable stop mechanism 79 includes an elbow portion 81 connected to the sleeve 80 and extending forwardly, whereat it is connected at its forward end to a stop member in the form of upper and lower pins 83 and 84. These pins are of such a height as to engage the adjacent vertebrae as the trial implant is moved into an intervertebral space therebetween. The elbow portion 81 has on its inner side a surface 82 which engages a side surface 85 of the tail section 76 such that the entire adjustable stop mechanism 79 is prevented from rotating about the axis of shaft 78.

Figure 17A:
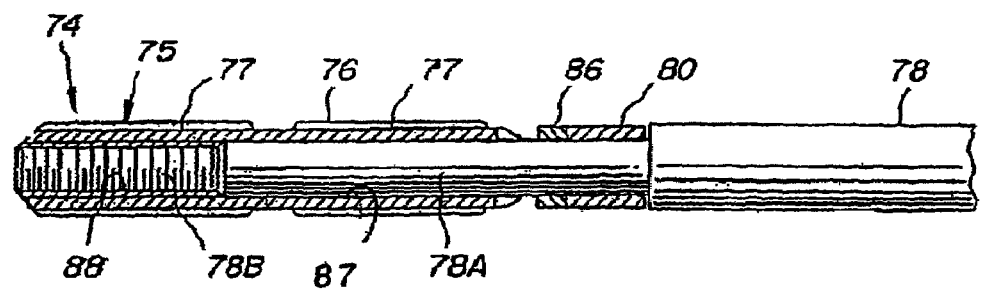
FIG. 17A is a central cross sectional view of FIG. 12.
Figure 17B:
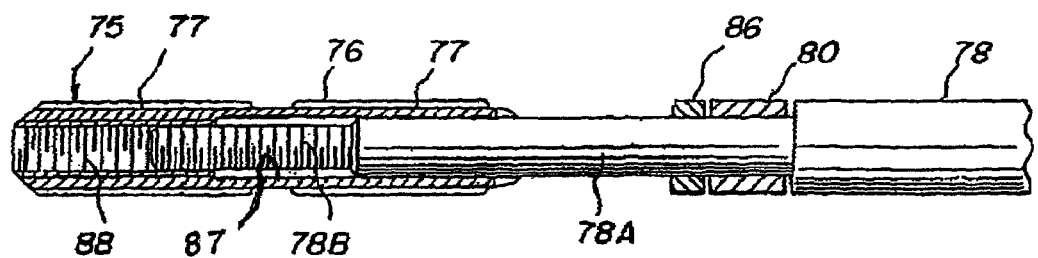
FIG. 17B is a central cross sectional view of FIG. 13.
Figure 19B:
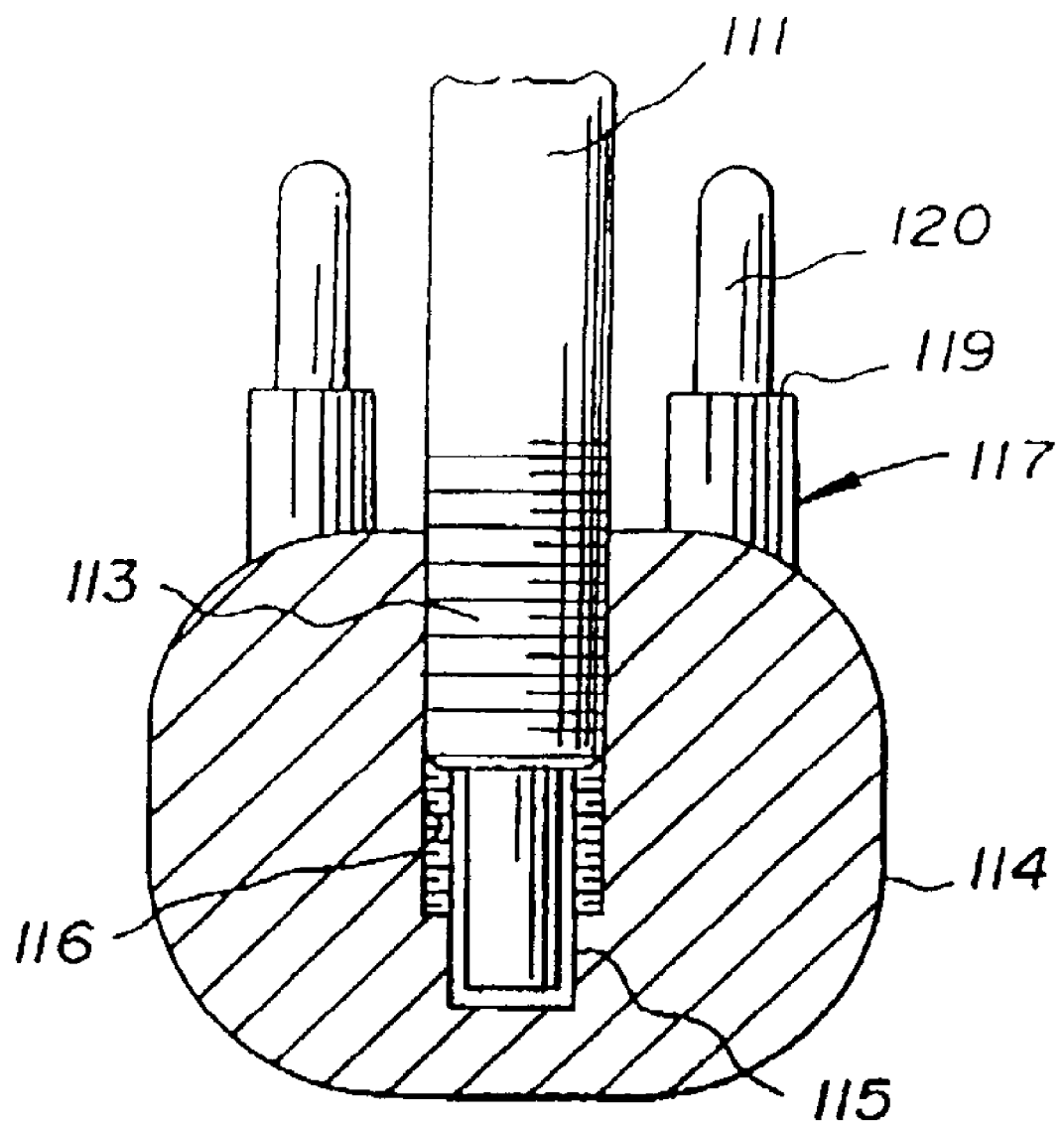
FIG. 19B is a cross sectional view of the trial implant shown in FIG. 19A.

Referring to FIGS. 16, 17A and 17B, the interior of trial implant 74 is hollow from end to end, including an enlarged unthreaded rearward bore 87 which steps down to a smaller threaded forward bore 88.

FIG. 17A shows the adjustable stop mechanism in its forwardmost position, wherein threaded section 78B is threaded completely into the bore 88. In this forwardmost position, the adjustable stop mechanism and hence the stop member are at their forwardmost position as shown in FIG. 12. The forward end of threaded section 78B is visible at the forward end of the body portion 75.

To move rearwardly from the forwardmost position of the adjustable stop mechanism and stop member toward the rearward position of FIG. 13, the operator would turn the shaft 78 to cause the threaded section 78B, via its engagement with the threaded forward bore 88 to move to the right. As the shaft 78 is rotated, its middle section 78A moves rotatably freely within the sleeve 80, wherein the adjustable stop mechanism 79 is prevented from rotating about the axis of shaft 78 by the engagement of its wall 82 with the side wall 85 of the tail section of the trial implant.

It will be seen that the adjustable stop mechanism of FIGS. 12-17B is somewhat simplified relative to the embodiment of FIGS. 3-11B since this embodiment utilizes the already existing shaft 78 and its bore in the trial implant without the necessity for a separate bore on the side of the trial implant and a separate tool for engaging the trial implant in that second bore.

The operation of the adjustable stop mechanism of FIGS. 12-17B is similar to operating the adjustable stop mechanism of FIGS. 3-11B in that the adjustable stop mechanism is first moved to a position where the upper and lower pins 83 and 84 of the stop member are located at their forwardmost position closest to the body portion, thus allowing only minimal movement of the body portion into the intervertebral space. As with the embodiment of FIGS. 3-11B, with the assistance of radiographic monitoring, the operator would then determine whether the trial implant had moved to its proper position. If not, the operator would then move the adjustable stop mechanism 79 rearwardly. In this embodiment, the operator would simply turn the main shaft 78, thus moving the forward shaft section 78B rearwardly by its threaded engagement with the threaded bore 88. During this movement, the engagement of walls 82 and 85 prevent rotation of the adjustable stop mechanism 79 about the axis of shaft 78 as the sleeve 80 is freely rotatably mounted thereon. As in the case of the embodiment of FIGS. 3-11B, with the assistance of radiographic monitoring, the operator would turn the shaft 78 in precisely defined amounts, for example one full turn equaling 1 mm in depth into the intervertebral space. FIGS. 13 and 17B represent an end position wherein the stop member has been pulled out and hence the body portion of the trial implant has been inserted into the intervertebral space to a desired position.

Figure 14:
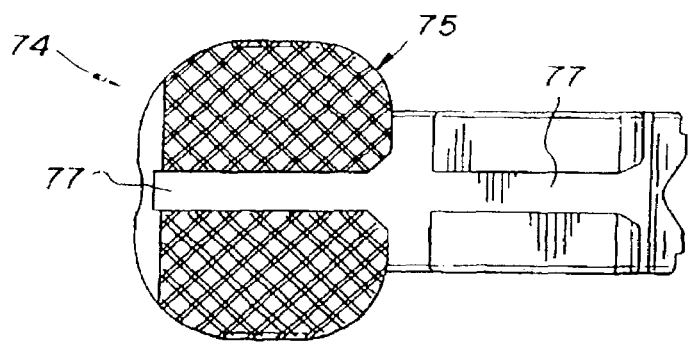
FIG. 14 is a plan view of the trial implant portion of FIG. 12.
Figure 14A:
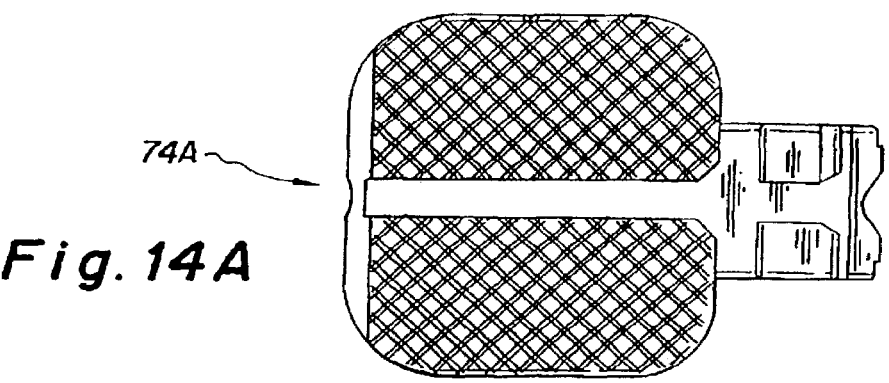
FIG. 14A is a plan view similar to FIG. 14, but of a trial implant of a different size.
Figure 15:
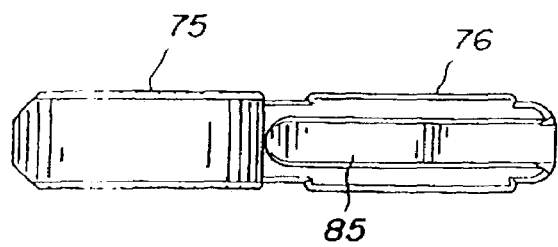
FIG. 15 is a side elevational view of FIG. 14.

It has been noted that the trial implant 74 of FIGS. 12-18 differs from the trial implant shown in FIGS. 3 and 4 (as well as the trial implants shown in FIGS. 19-35) in that the former has a tail section. As described above, this tail section functions to provide one embodiment of an adjustable stop mechanism. This tail section has a second function. As described more fully below with respect to the embodiment shown in FIGS. 36-43, the tail section allows a single chisel cutting tool to be usable with a plurality of different trial implants, all having the same height but having body portions of different surface areas. For example, by comparing the trial implant 74 of FIG. 14 with the trial implant 74A of FIG. 14A, it will be seen that the trial implant 74 of FIG. 14 has a body portion with a smaller surface area than the body portion of trial implant 74A of FIG. 14A; and the trial implant 74 of FIG. 14 also has a longer tail section than that of trial implant 74A of FIG. 14A, wherein both of the trial implants are of the same overall length.

FIG. 18 illustrates a chisel cutting tool similar to that described in FIGS. 36-43, but adapted especially for use with the trial implant and adjustable stop mechanism 79 of FIGS. 12-17B.

Figure 41:
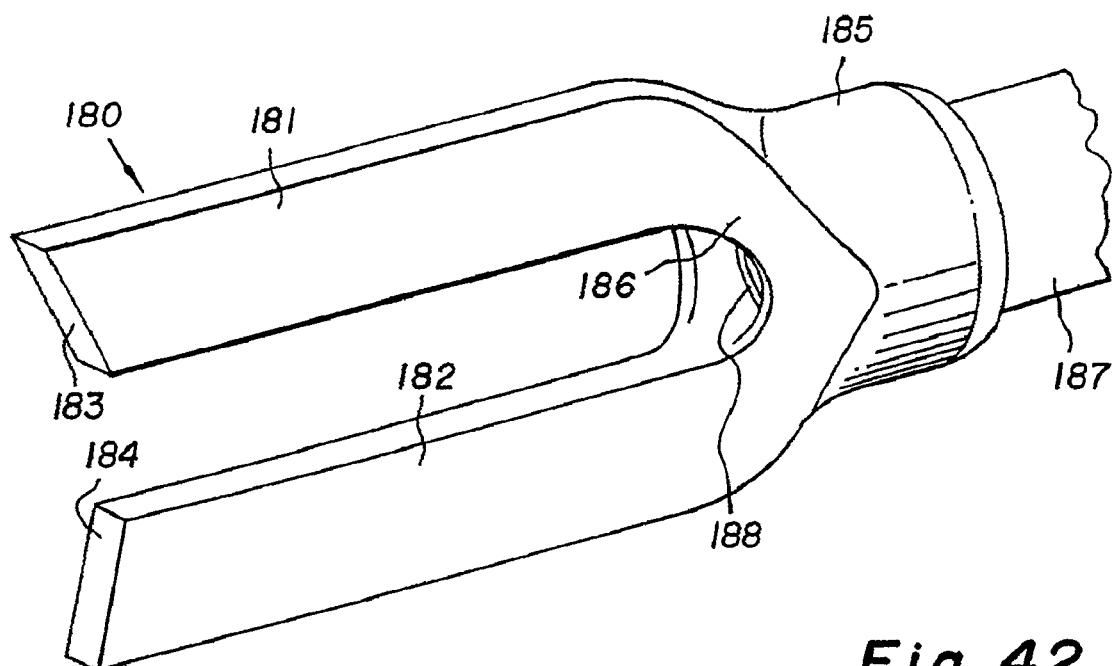
FIG. 41 is a perspective view of a chisel for use with the instrument and trial implant shown in FIGS. 36-40.
Figure 42:
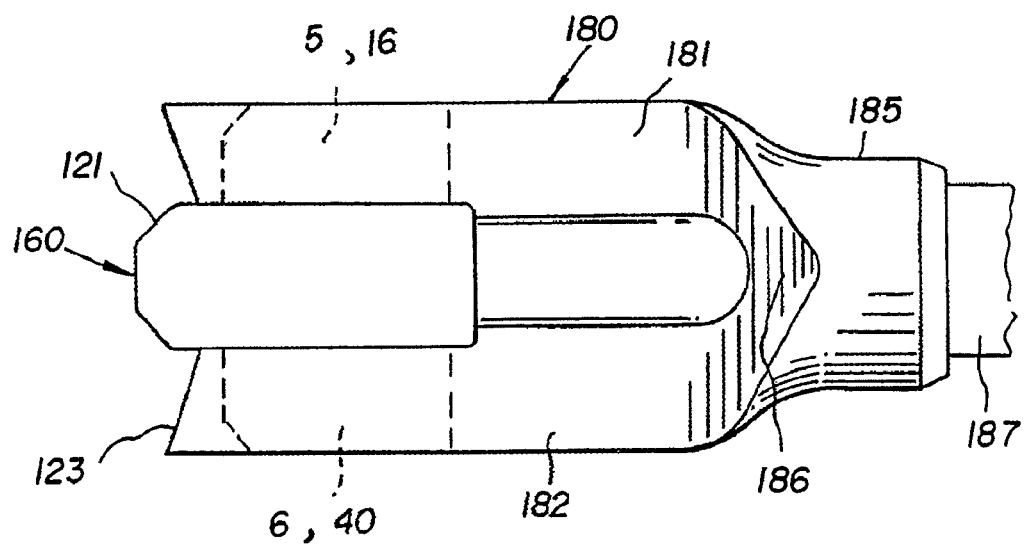
FIG. 42 is a side elevational view showing the modified trial implant and the chisel mounted thereon.
Figure 43:
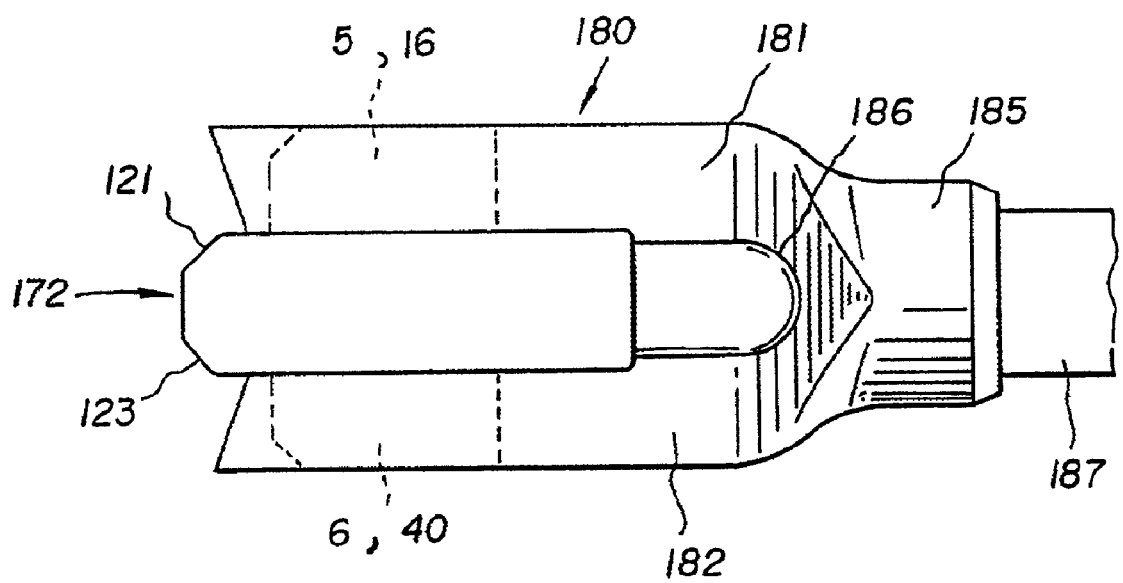
FIG. 43 is a side elevational view similar to FIG. 42 but showing a different size trial implant.

Referring to FIG. 18, there is shown superimposed on the trial implant 74 a chisel cutting tool 90 having an upper cutting arm 91 with a box cut front cutter 92 and a lower arm 93 with a box cut front cutter 94. The chisel cutting tool shown and described below with respect to FIGS. 41-43 may have a box cutting edge as shown herein or the embodiment shown in FIG. 18 may have a more standard forward cutting edge as shown in FIGS. 41-43. Unlike the chisel cutting tool shown in FIGS. 41-43, the chisel cutting tool 90 of FIG. 18 has an elongated collar 96 having a slot 97 therein for receiving the adjustable stop mechanism 79. This collar 96 terminates at its forward end at a throat 95, similar to that shown in FIGS. 41-43 which engages the V-shaped indentation at the rear of the trial implant 74. As in the case of FIGS. 41-43, the upper and lower arms 91 and 93 engage and move along the upper and lower slots 77 in the trial implant 74. In the embodiment of FIG. 18, the rear end of collar 96 is connected to a hollow shaft 98 which surrounds the shaft 78 so that the entire unit 90 including the arms, collar and hollow shaft 98 can move over the shaft 78 and forwardly all the way to the position shown in FIG. 18. As noted above, this exact chisel cutting tool will fit both the trial implant 74 shown in FIGS. 12-15, 17A and 17B, and the different size trial implant 74A of FIG. 14A.

FIGS. 19-23 illustrate another improvement in instruments and methods for inserting a trial implant.

Figure 22:
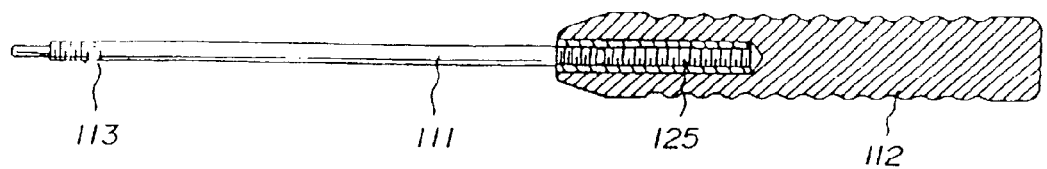
FIG. 22 is a cross sectional view of a tool which is a part of FIG. 19.
Figure 23:
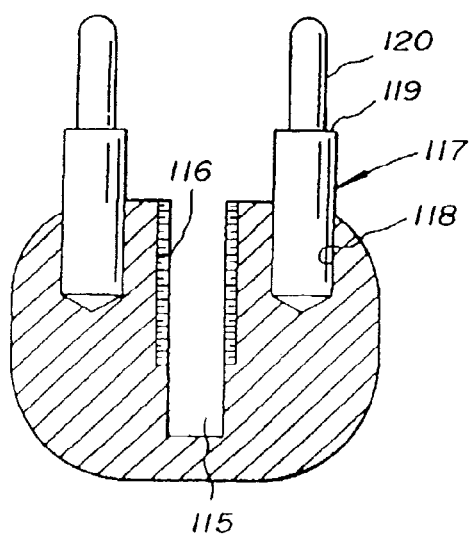
FIG. 23 is a cross sectional view of the trial implant taken along line 23-23 of FIG. 21.
Figure 24:
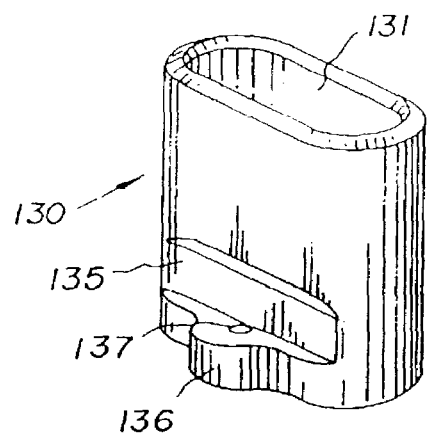
FIG. 24 is a perspective view of a burr guide.

Referring to FIGS. 19-23, the trial implants are held on a holding device in the form of a tool 110 which has a rod 111 and a handle 112 threaded thereon. At its operative end, as shown in FIG. 22, this insertion tool includes a threaded portion 113.

The trial implants 114 comprise a slot 115 with an internally threaded portion 116 which threadedly receives the threaded portion 113 of the insertion tool 110. Referring to FIGS. 20 and 21, the trial implants include a first generally flat surface 122 and a second generally flat surface 123. The posterior end thereof includes a pair of bevels 121 and 124.

Each trial implant 114 is provided with a pair of guide pins 117. See FIGS. 19, 21 and 23. These guide pins 117 are received in a recess 118 in the trial implant 114 and they include a shoulder 119 and a narrow free end 120.

After the intervertebral space has been prepared, the user determines the trial implant which appears most likely to fit perfectly within the intervertebral space. That trial implant is threaded onto the end of shaft 111 of trial insertion tool 110, after which that trial implant is inserted. By trial and error, the operator will eventually be able to select the correct one of the trial implants for that intervertebral space, which of course will then be used to select the actual implant to be inserted into that intervertebral space.

Once the correct trial implant has been selected, the next step is to form the cutouts in the adjacent vertebrae.

The preceding discussion has referred to trial implants of a fixed height, wherein a set would include a plurality of trial implants of different heights. However, in practice it is also possible to provide trial implants which are adjustable in height.

Figure 25:
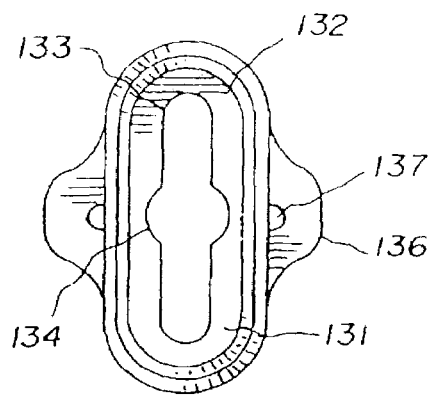
FIG. 25 is a top plan view of the burr guide shown in FIG. 24.
Figure 26:
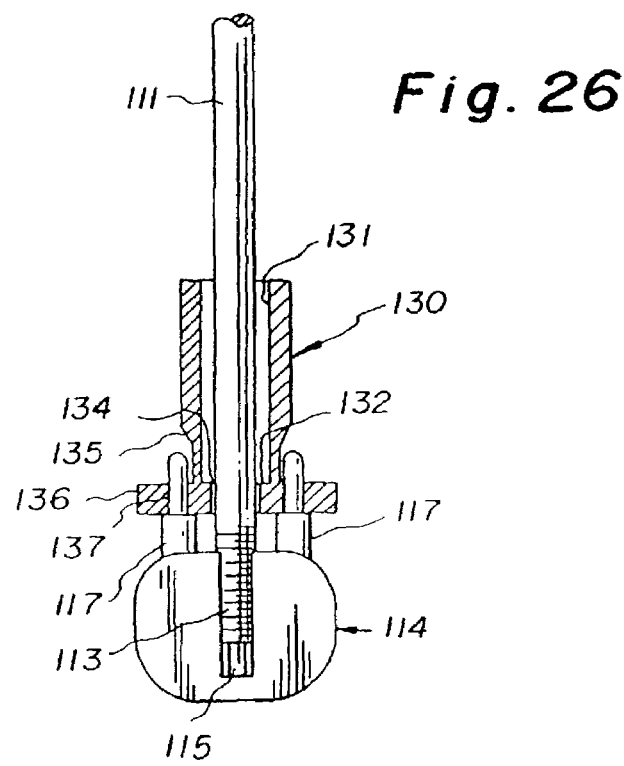
FIG. 26 is a cross sectional view of the tool of FIG. 19 showing the burr guide mounted on the trial implant.
Figure 30:
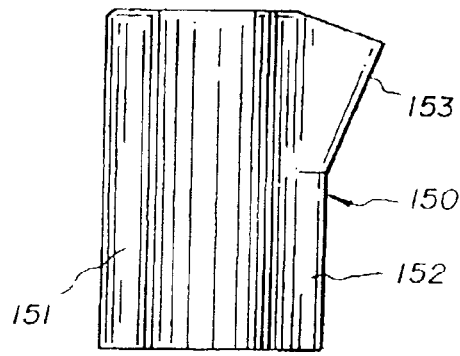
FIG. 30 is a side elevational view of another embodiment of a burr guide.
Figure 31:
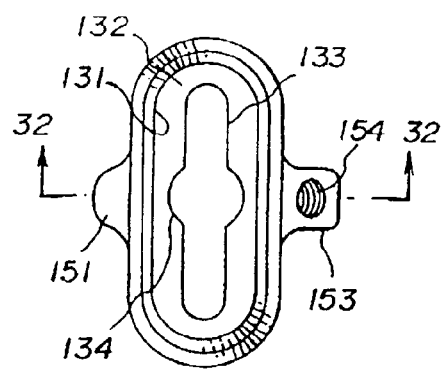
FIG. 31 is a top plan view of FIG. 30.
Figure 32:
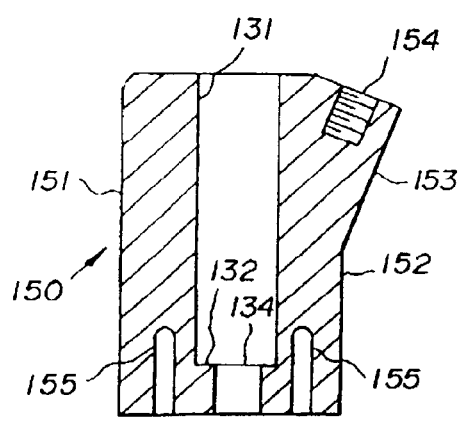
FIG. 32 is a cross sectional view taken along line 32-32 of FIG. 31.

A first embodiment of instruments for forming the cutouts are shown in FIGS. 24-29. Once the correct trial implant has been selected, it is placed within the intervertebral space while mounted on shaft 111 of the insertion tool 110. The handle 112 is then removed by being unscrewed from shaft 111. A guide 130 is then slid down along the shaft 111. The guide is shown in detail in FIGS. 24 and 25. It includes an elongated slot 131 extending for most of the height of the guide 130 down to a bottom ledge 132 which has an elongated opening or slot 133 with an enlarged rounded central opening 134. Guide 130 includes a pair of recesses 135 in the long sides thereof with lugs 136 projecting outwardly below these recesses and with pin holes 137 extending through the lugs 136. As best shown in FIG. 26, the guide 130 is slid along shaft 111 until the pins 117 pass through the openings 137 with the lower ends of the lugs 136 resting on the shoulders 119. The spacing along the pins 117 from the surface of the trial implant 114 to the shoulders 119 is selected such that the guide 130 will come to rest at a very precise location spaced a predetermined distance from the trial implant 114. This spacing will assure that the guide 130 will not touch the surface of the vertebrae and it will serve as a reference point for the depth of a cutting tool, as described below.

Once the guide is in place, the shaft 111 is removed from the trial implant 114 and the guide 130 by being turned such that its threads 113 disengage from the threads 116 in the trial implant 114. Thereafter, a cutting tool is inserted. The cutting tool can take different forms. For example it may be a chisel cutting tool which would be guided in elongated slot opening 133. In the alternative, the cutting tool could be a burr cutting tool which would be guided by the elongated slot opening 133. Referring to FIG. 27, a burr cutting tool 140 includes an upper rod portion 141 which is integral with its lower portion 144 and with fixed collar 142. A hollow spacer sleeve 143 is then slid onto the burr 140 from the end of lower portion 144 until its upper end engages the fixed collar 142. Referring to FIG. 28, the burr includes a bump 145 thereon and the spacer sleeve 143 includes an internal circumferential groove 146 which, at any circular orientation of the spacer sleeve 143 will receive the bump 145 to fix the spacer sleeve 143 against unintended vertical movement along the burr 140. The length of sleeve 143 determines the exact depth of the lower portion 144 of the burr into the slot 115 which in turn determines the depth that the burr lower portion 144 will extend into the adjacent vertebrae as it subsequently forms the cutouts. This fixed depth setting of the burr is apparent from FIG. 29 wherein it is seen that the lower end of the spacer sleeve 143 abuts the ledge 132 of the guide 130. Referring to FIG. 25 as well as FIG. 29, with the burr 140 positioned as shown in FIG. 29, with the bottom of the spacer sleeve 143 resting on ledge 132, the exact depth of the end of the burr is determined. Referring to FIG. 25, it can be seen that with the burr positioned as shown in FIG. 29, the end of the burr is free to move up and down in the elongated opening 133. The burr is driven by a power means, not shown, both in rotation and laterally up and down the elongated opening 133. This movement then forms the cutouts in the vertebrae.

FIGS. 30-33 show another embodiment 150 of a guide for a cutting tool. Elements therein which are common to the embodiment of FIGS. 24-26 have common reference numerals. In this embodiment, the guide 150 includes, in place of the recesses 135 and lugs 136 a pair of central ridges 151 and 152 which run along the center outside of the wide sides of the guide 150. At its lower ends, guide 150 is provided with a pair of pin holes 155 which are sufficiently deep to receive the pins 117 of the trial implant 114. In accordance with another feature of guide 150, one of the central ridges is enlarged as shown at 153 to form an angled boss which has a threaded hole 154 therein constructed to receive the threaded end 113 of a tool 110. This embodiment is particularly suitable for those users of the instruments who might prefer to positively engage and move the guide, rather than permit it to fall by gravity onto the pins 117. Also, in specific situations, it may be necessary to utilize a tool 110 for positively locating the guide rather than allowing it to fall in place by gravity.

Figure 33:
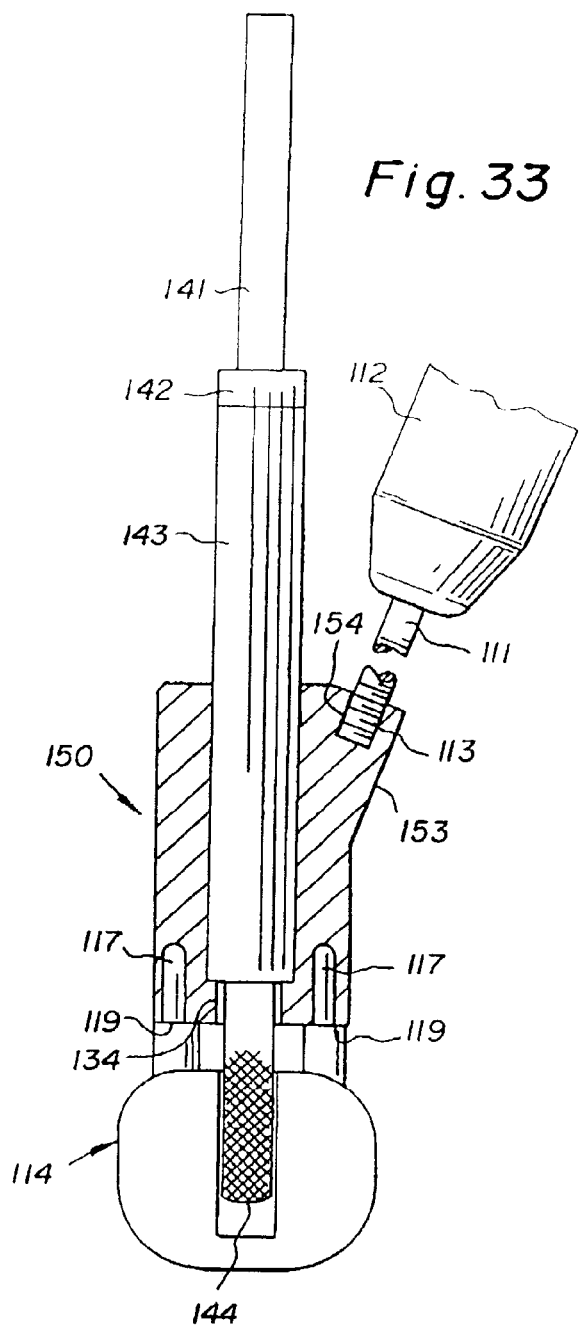
FIG. 33 is a cross sectional view showing the trial implant and the burr guide of FIGS. 30-32, together with the burr of FIG. 27.
Figures 36, 36A:
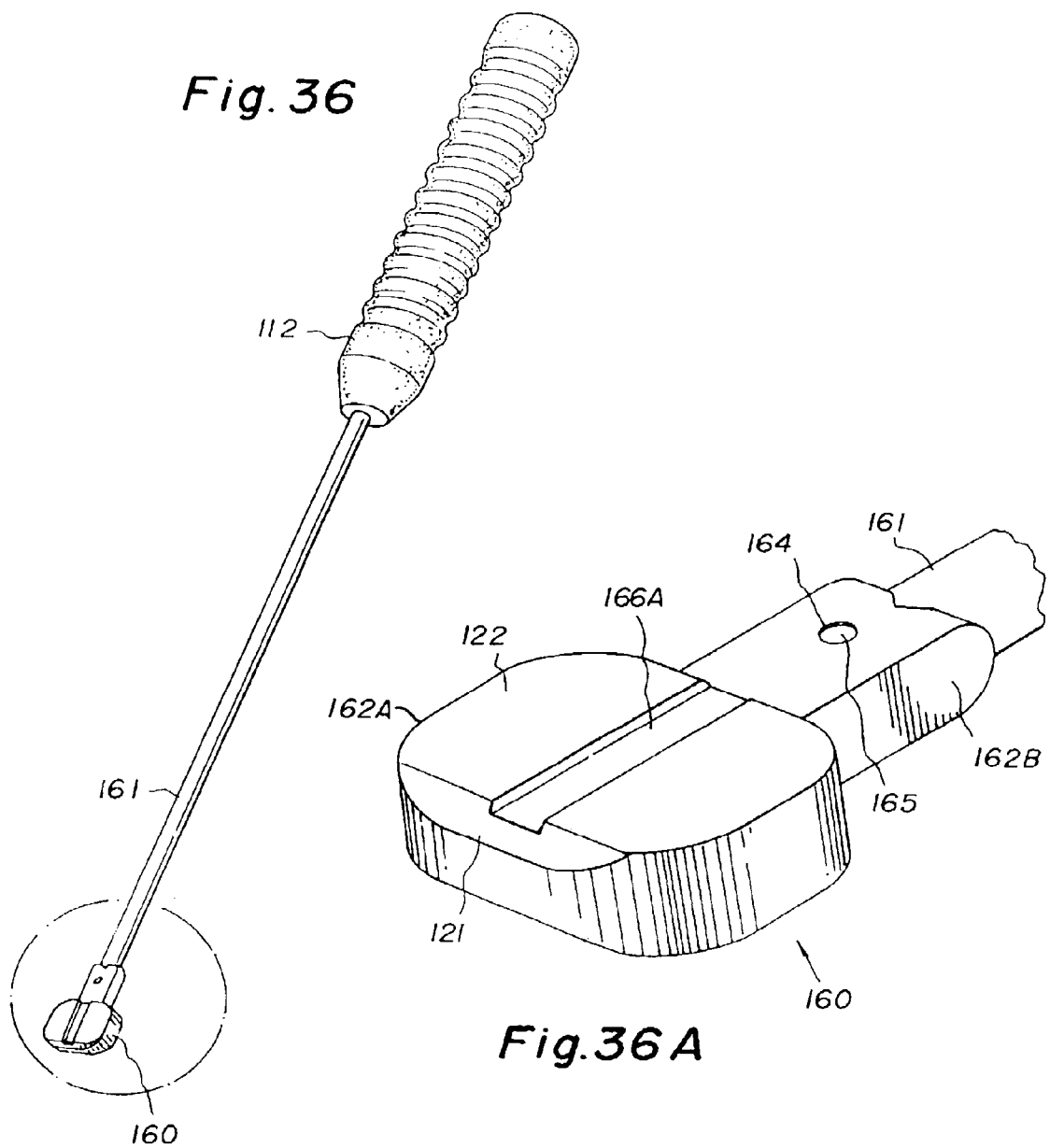
FIG. 36 is a perspective view illustrating another embodiment of an instrument for inserting trial implants and another embodiment of a trial implant.
FIG. 36A is an enlarged perspective view of the portion of FIG. 36 shown in the broken line circle.

FIG. 33 shows this guide 150 mounted on pins 117 and resting on shoulders 119 thereof of the trial implant 114. In other respects, the arrangement of FIG. 33 is similar to FIG. 29 in the manner that a burr 140 with the spacer sleeve 143 thereon are received within the guide 150. Also, as with the earlier embodiment, a chisel cutting tool can be used with guide 150.

FIGS. 34 and 35 show another embodiment of a spacer sleeve. As shown therein, the spacer sleeve 158 includes a tapered upper portion 158 forming at its lower end a circular shoulder 159 surrounding a cylindrical lower portion 160 which would be of essentially the same diameter as the spacer sleeve 143 of burr 140. This spacer would also include the bump and groove structure shown in FIG. 28. The advantage of this spacer sleeve is that the shoulder 159 will ride along the top of the guide. This has been found to provide greater stability than when relying only on spacer sleeve 143 riding along ledge 132. It has been found that by using the burr 140 and relying for stability only on contact between the lower end of spacer sleeve 143 and ledge 132, the burr might tend to wobble somewhat. However, by relying also on an engagement between the shoulder 159 of spacer sleeve 157 and the top edge of the guide, there is less of a tendency for the burr to wobble.

Although the spacer sleeve of FIG. 34 is shown in FIG. 35 with the first embodiment 130 of the guide, it is to be understood that it is equally applicable for use with the guide 150 shown in FIGS. 30-33.

The preceding discussion of cooperating trial implants with pins cooperating with guides with apertures may be reversed in that the pins may be provided on the guides and the apertures formed in to the trial implants.

FIGS. 36-43 show another embodiment of a trial implant and another embodiment of an instrument for forming the cutouts in the vertebrae. Referring to FIGS. 36-40, the trial implants 160 are shaped somewhat differently than the trial implants 114. These trial implants 160 are similar to trial implants 114 in that they are preferably provided in the same number of sizes, and they include upper and lower surfaces 122 and 123 and bevels 121 and 124. They are also similar to the trial implants shown in FIGS. 12-18, but without the adjustable stop mechanism feature.

However, the trial implants 160 differ from trial implants 114 in several respects. First, slots 166A and 166B are formed along the top and bottom, respectively, of the trial implants 160 as shown in FIGS. 36-40 and for a purpose to be discussed below. Trial implants 160 include a main body portion 162A and a tail section 162B with an elongated opening 163 and pin holes 164 in the top and bottom thereof. The insertion tool 161 includes a holding device which may comprise a threadedly removable handle 112 and a shaft 161. Shaft 161 may be threadedly engaged with the different trial implants as shown in FIGS. 19-23. However, as an alternative, the shaft 161 may differ from shaft 111 of FIG. 19 in that the end of this shaft 161 may engage the opening 163 and instead of being threaded, include a through pin hole 168. To engage the trial implant 160, the shaft 161 is pushed into the opening 163 in the tail section 162B until the pin hole 168 lines up with the pin holes 164. With shaft 161 thus positioned within the opening 163 of tail section 162B, a pin 165 is passed through the openings 164 and 168 to secure the shaft 161 onto the trial implant 160. Since this is an essentially permanent connection between the shaft 161 and the trial implant 160, it means that as a general rule, each of the 15 trial implants will have a shaft fixed thereto. However, since the shafts 161 without the large handles 112 thereon are relatively small and economical, it is feasible to have a separate shaft fixed to each of the plurality of trial implants 160 of the set, as opposed to using a single shaft 161 for all trial implants 160 of the set.

The purpose of this alternative embodiment 160 of the trial implant is to cooperate with the cutting tool in the form of a chisel 180 as shown in FIGS. 41-43 form the cutouts in the vertebrae with a chisel rather than by a burr. The chisel includes an upper chisel arm 181 with a sharp end 183 and a lower arm 182 with a sharp end 184. Referring to FIGS. 42 and 43, once the correct trial implant 160 has been selected, the chisel 180 is moved onto the trial implant 160, moving over the shaft 161 with the facing edges of the arms 181 and 182 engaging within the slots 166A and 166B formed along the top and bottom of the trial implant 160.

The present embodiment of a chisel for forming the cutout is provided because in many instances the user will prefer to use a chisel to form the cutouts rather than a power driven burr.

As noted earlier, a plurality of trial implants are provided, i.e., in different surface areas and each of those in different heights. An advantage of the present embodiment is that a single chisel can be used for all trial implants with differing surface areas and having the same height. This is accomplished by having different size tail sections, i.e., the smaller surface areas would have a larger tail section so that the total distance of the chisel in engagement with the trial implant 160 will be the same for all trial implants having the same surface area.

Referring to FIG. 41, each chisel includes a V-shaped base 186 forward of an enlarged section 185 which receives a hollow shaft 187. To install the chisel onto a trial implant 160, the chisel would be moved onto the trial implant with the attached shaft 161 moving into opening 188 and through the hollow chisel shaft 187. When in place with the facing surfaces of arms 181 and 182 positioned within slots 166A and 166B, the V-shaped portions 186 would fit into the V-shaped end 169 as shown in FIG. 39.

The arrangement which permits a given chisel to fit all trial implants having the same height, and differing surface areas, can be illustrated with respect to FIGS. 39 and 40. Trial implant 172 of FIG. 40 has a larger surface area than trial implant 160 of FIG. 39. It therefore has a shorter tail section 173. The result is that the distance from the front end of trial implant 160 to the base 170 of the V-shaped end 169 is the same as the distance from the front end of the trial implant 172 of FIG. 40 to the base 175 of the V-shaped end 174. This is also illustrated by comparing FIGS. 41 and 42 which show how a given chisel 180 will fit onto the trial implant 160 and the trial implant 172.

FIGS. 42 and 43 also illustrate an outline where the upper and lower keels, such as 5 and 6 in FIG. 1 or 16 and 40 in FIG. 2, will ultimately be located, relative to the cutouts formed by these chisels. These chisels will form cutouts with interior posterior ends which may be angled back. The ends of the chisel arms can also be straight up and down (neutral) rather than angled back.

The preceding discussion of the chisel cutting tools has described a pair of cutting tools, one above and one below the trial implant. It is also possible to utilize a chisel having only one arm for forming a cutout in only one vertebrae or for forming two cutouts in the two adjacent vertebrae one at a time.

Figure 44:
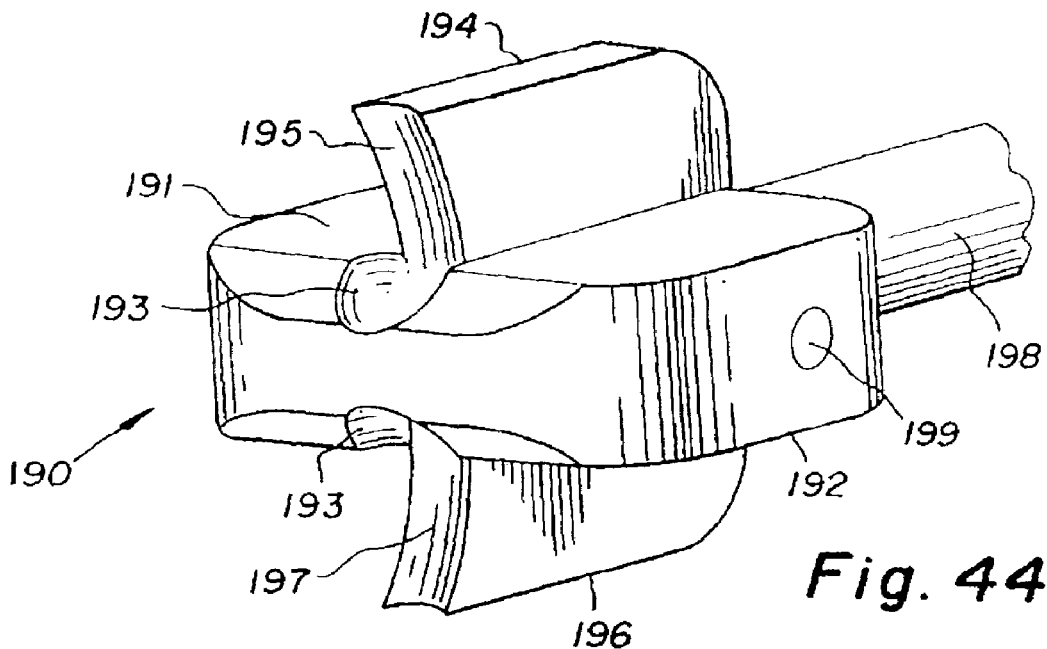
FIG. 44 is a front perspective view of another embodiment of a cutting tool.
Figure 45:
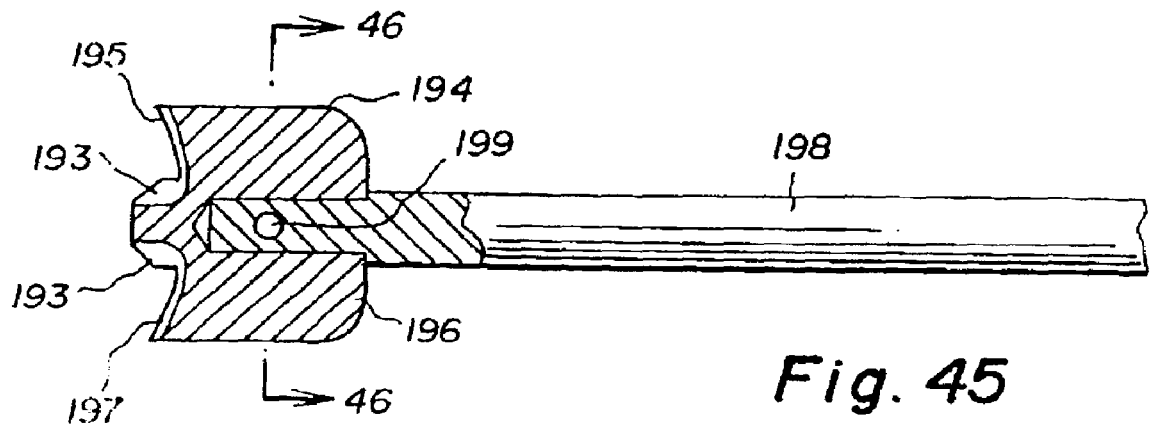
FIG. 45 is a longitudinal sectional view of the cutting tool of FIG. 44.
Figure 46:
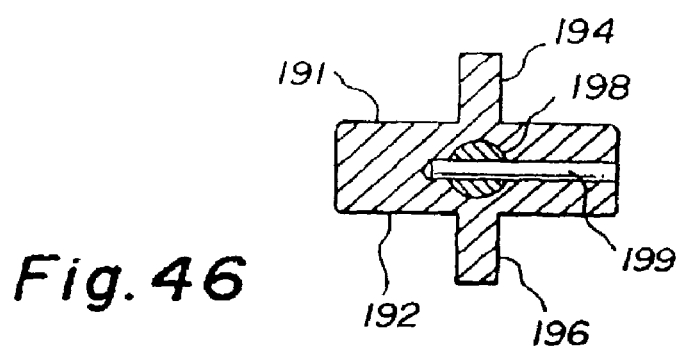
FIG. 46 is a cross sectional view taken along line 46-46 of FIG. 45.

FIGS. 44-46 illustrate another embodiment of a chisel cutting tool for forming the cutouts in the adjacent vertebrae.

FIGS. 44-46 show a trial implant/cutting tool 190 which has a body portion having an upper surface 191 and a lower surface 192 and having upper and lower chisel arms 194 and 196 affixed thereto and extending upwardly and downwardly therefrom. The front edges of these upper and lower arms include cutting edges 195 and 197, respectively. Forward of these cutting edges there are provided upper and lower scoop recesses 193 for receiving the cut bone chips. A holding device in the form of a shaft 198 extends into the center of the trial implant shaped chisel cutting tool 190, and is fixed therein by a cross pin 199.

In the alternative, the fixed shaft 198 can be replaced by a shaft having a threaded end which would be threadedly and hence removably attached to the main portion of cutting tool 190. Also, the embodiments of FIGS. 44-46 could be made with a single chisel arm rather than two chisel arms, which tool could then be used to cut only a single cutout in one vertebrae or to form a cutout in two adjacent vertebrae, one at a time.

The embodiment of FIGS. 44-46 can be used in different ways. First, the operator can use conventional trial implants and then, after the correct size trial implant has been determined, use the tool 190 with a body portion of the same size as the selected trial implant, to form the cutouts. Second, the tool 190 can be used as the actual trial implant. Here, as the operator tests the body portion, the chisel arms would cut the vertebrae to form the cutouts.

Although the method of preparing an intervertebral space for receiving an implant will be apparent from the preceding discussion of the instruments, there follows a brief summary of the method of the present invention.

After the relevant intervertebral space has been cleaned out, in accordance with a first method of the present invention, trial implants having an adjustable stop mechanism are inserted into the intervertebral space, continuing to try different size trial implants of the set thereof, until the correct size trial implant has been selected. In the past, these trial implants have had a fixed stop member for limiting movement of the initial, subsequent or final trial implant into the intervertebral space. According to the method of the present invention, each trial implant has an adjustable stop mechanism. When a given trial implant is moved into the intervertebral space, the stop member of the adjustable stop mechanism will preferably initially be located in its position closest to the back of the body portion of the trial implant, thus allowing minimum movement of the body portion of the trial implant into the intervertebral space. If the vertebrae adjacent the space is perfectly formed, the body portion of the trial implant may move to the correct position within the intervertebral space with the initial setting of the adjustable stop. However, if the vertebrae has an irregularity and/or if there is a bone spur preventing movement of the body portion, then, with the benefit of radiographic monitoring, the operator observes the position of the trial implant within the intervertebral space. If the trial implant has not moved to the proper position, the operator moves the adjustable stop mechanism and hence its stop member rearwardly away from the back of the body portion of the trial implant, thus allowing further movement of the body portion of the trial implant into the intervertebral space. The adjustment range may allow insertion of between 1 and 10 mm into the intervertebral space. A precise manual control may be provided.

In one embodiment, a rotatable tool such as a screwdriver, wrench or the like is received in a socket or the like in the adjustable stop mechanism and calibrated such that one 360° turn can equal 1 mm of movement of the stop member and hence of depth of the trial implant. In accordance with this method of the present invention, the stop member is freely rotatably mounted on a adjustment member but includes a lug which engages a slot on the side of the trial implant, thus preventing rotational movement of the stop member while the operator turns the adjustable member on which it is mounted, wherein the latter threadedly engages the interior of the body portion of the trial implant, the result being that by turning the adjustable member, the assembly of the stop member and the adjustment member are moved in and out of the trial implant (or in the case of the stop member towards and away from the back of the body portion of the trial implant), with the stop member fixed against rotational movement.

In another embodiment, an adjustable stop mechanism is located along the side of a tail section of a trial implant, behind the body portion of the trial implant, while a sleeve thereof, located around a 90° elbow is freely rotatably mounted on the main shaft of the trial implant which is threadedly engaged within the interior of the trial implant. In this case, simply turning the main shaft of the trial implant moves the adjustable stop mechanism, and hence its stop member, towards and away from the rear of the body portion of the trial implant. This embodiment, like the first described embodiment, can be calibrated such that one 360° turn of the main shaft can equal 1 mm of movement of the stop member and hence the depth of the trial implant. Engagement of a side wall of the adjustable stop mechanism with a side wall of the tail section of the trial implant prevents rotational movement of the adjustable stop mechanism about the axis of the main shaft.

In accordance with another method of the present invention, a trial implant is threaded onto a holding device such as a handle and inserted into the intervertebral space. If the initial trial implant is not a perfect match for the intervertebral space, then other trial implants will be tried until, through trial and error, the trial implant of the correct size has been determined. Assuming that the trial implant has a stop member mounted thereon, the handle is then threaded off of the trial implant and a guide is moved down over the shaft until the two openings in guide or the lower ends of pin holes in guide are received on the pins, further downward motion then being limited by engagement of the bottom of guide on the shoulders. Thereafter, the shaft is removed and a cutting tool, which may be a burr or a chisel, is inserted through an elongated slot opening in the bottom of the guide. If the cutting tool is a burr, it includes a fixed collar and a carefully selected spacer sleeve mounted thereon which are inserted into the guide until the bottom of the spacer sleeve engages the ledge or the shoulder of spacer sleeve has engaged the top of the guide. The length of the spacer sleeve has been selected so that when it engages the ledge or the shoulder of spacer sleeve has engaged the top of the guide, the lower end of the burr will project downwardly for a precisely determined distance, which in turn will determine the depth of the cutout into the vertebrae.

Next, power means are applied to the burr to rotate it about its axis and move it vertically so that it travels up and down along the elongated slot opening. The end limits of the elongated slot opening will determine the limits of the cutouts in the vertical direction.

According to an alternate method, a holding device such as a shaft is inserted into an opening within a tail section of trial implant and secured therein. As in the previous embodiment, there will be an entire set of a plurality of trial implant sizes.

After the correct trial implant has been selected, a chisel is mounted onto the selected trial implant with the inner edges of its arms engaging slots in the top and bottom of the trial implant. Thereafter, the trial implant is moved into the intervertebral space, and as it so moves, the sharp edges of the chisel cut into the vertebrae, forming the cutouts.

In accordance with another method of the present invention, the operator would utilize a cutting tool having a body portion shaped like the body portion of a trial implant but having one or two chisel arms fixed thereto. The operator could proceed in one of two ways. First, the operator can use conventional trial implants and then, after the correct size trial implant has been determined, use the tool with a body portion of the same size as the selected trial implant, to form the cutouts. Second, the tool can be used as the actual trial implant. Here, as the operator tests the body portion, the chisel arms would cut the vertebrae to form the cutouts.

Although the invention has been described in considerable detail with respect to preferred embodiments thereof, it will be apparent that the invention is capable of numerous modifications and variations, apparent to those skilled in the art.

What is claimed is:

1. A device for preparing an intervertebral space, which device includes an operative portion to be inserted into an intervertebral space, an adjustable stop mechanism which includes a stop member located rearward of the operative portion and having a height great enough to engage a vertebrae as the operative portion moves into the intervertebral space, the adjustable stop mechanism being adjustable to change the distance between the back of the operative portion and the stop member to change the insertion distance that the operative portion can move into the intervertebral space, the adjustable stop mechanism connected to the operative portion by a threaded engagement which threadedly connects the adjustable stop mechanism to the operative portion such that relative movement of the threaded engagement between the adjustable stop mechanism and the operative portion in one direction moves the stop member toward the operative portion and relative movement of the said threaded engagement in the opposite direction moves the stop member away from the operative portion, the stop member mounted to freely rotate on a threaded member of the adjustable stop mechanism, and including an abutment surface of the operative portion which prevents the stop member from rotating about the axis of the threaded member, whereby, upon relative movement between the threaded member and the operative portion, by relative movement of the threaded engagement the stop member moves toward and away from the rear of the operative portion without rotating about the axis of the threaded member.

2. A device according to claim 1, including a bore extending through the operative portion, a portion of the bore being threaded and forming a part of said threaded engagement.

3. A device according to claim 2, the adjustable stop mechanism comprising an adjustment member which has the threaded portion thereon, wherein the stop member is mounted on the adjustment member so as to be freely rotatable thereon but restricted against longitudinal movement therealong.

4. A device according to claim 3, wherein the operative portion and the stop member engage each other to prevent rotation of the stop member and maintain it in a certain rotatable position wherein one or more arms of the stop member are in a vertical position so as to engage a vertebrae as the operative portion moves into the intervertebral space.

5. A device for preparing an intervertebral space, including a shaft having at the end thereof an operative portion to be inserted into an intervertebral space, an adjustable stop mechanism which includes a stop member located rearward of the operative portion and having a height great enough to engage a vertebrae as the operative portion moves into the intervertebral space, the adjustable stop mechanism being adjustable to change the distance between the back of the operative portion and the stop member to change the insertion distance that the operative portion can move into the intervertebral space, the adjustable stop mechanism connected to the operative portion by a threaded engagement which threadedly connects the adjustable stop mechanism to the operative portion such that relative movement of the threaded engagement between the adjustable stop mechanism and the operative portion in one direction moves the stop member toward the operative portion and relative movement of the said threaded engagement in the opposite direction moves the stop member away from the operative portion; and a threaded end of the shaft and the operative portion forming said threaded engagement, the adjustable stop mechanism being mounted on the shaft for free rotation therearound but restricted against movement longitudinally therealong.

6. A device for preparing an intervertebral space, which device includes a trial implant, which trial implant comprises a body portion of a shape adapted to fit into an intervertebral space, an adjustable stop mechanism which includes a stop member located rearwardly of the body portion and having a height great enough to engage a vertebrae as the body portion moves into the intervertebral space, the adjustable stop mechanism being connected to the trial implant by a threaded engagement, such that relative movement of the threaded engagement between the adjustable stop mechanism and the trial implant in one direction moves the stop member toward the body portion and relative movement of the said threaded engagement in the opposite direction moves the stop member away from the body portion to thereby change the insertion distance that the body portion of the trial implant can move into the intervertebral space, the stop member mounted to freely rotate on a threaded member of the adjustable stop mechanism, and including an abutment surface of the trial implant which prevents the stop member from rotating about the axis of the threaded member, whereby, upon relative movement between the threaded member and the trial implant, by relative movement of the threaded engagement the stop member moves toward and away from the rear of the body portion without rotating about the axis of the threaded member.

7. A device according to claim 6, including a bore extending through the trial implant, a portion of the bore being threaded and forming a part of said threaded engagement.

8. A device according to claim 6, the trial implant including front to rear slots at least on one of the top and bottom thereof and adapted to receive a cutting tool.

9. A device according to claim 6, comprising a bore formed into the back of the trial implant, the adjustable stop mechanism being moveable into and out of the bore to change the said insertion distance.

10. A device according to claim 9, the bore having a threaded portion which engages a threaded part of the adjustable stop mechanism.

11. A device according to claim 10, the adjustable stop mechanism comprising an adjustment member which has the threaded portion thereon, wherein the stop member is mounted on the adjustment member so as to be freely rotatable thereon but restricted against longitudinal movement therealong.

12. A device according to claim 11, wherein the body portion and the stop member engage each other to prevent rotation of the stop member and maintain it in a certain rotatable position wherein one or more arms of the stop member are in a vertical position so as to engage a vertebrae as the trial implant moves into the intervertebral space.

13. A device according to claim 12, wherein the body portion includes a slot adjacent the bore, and the stop member includes a projection which is received in the slot to prevent rotation of the stop member and maintain it in a proper rotative orientation with the arm or arms projecting vertically.

14. A device according to claim 11, wherein the adjustment member includes a structure at the rear end thereof to receive a tool to turn the adjustment member.

15. A device according to claim 11, wherein the adjustment member includes a central smooth shaft of lesser cross section than the threaded portion and an enlarged member spaced from the threaded portion, and the stop member including a sleeve rotatable on the smooth shaft between the threaded portion and the enlarged member and a pair of arms extending in opposite directions from the sleeve.

16. A device according to claim 15, wherein the body portion includes a slot adjacent the bore and the stop member includes a projection which is received in the slot to prevent rotation of the stop member and maintain a proper orientation of both of said arms projecting vertically.

17. A device according to claim 6, including a shaft having a threaded end threadedly engaged in the trial implant, the adjustable stop mechanism being mounted on the shaft for free rotation therearound but restricted against movement longitudinally therealong.

18. A device according to claim 17, the implant having a tail section narrower than the body portion, and the adjustable stop mechanism comprising a stop member which moves along the side of the tail section toward and away from the body portion.

19. A device according to claim 18, wherein the adjustable stop mechanism engages the side of the tail section to prevent rotation of the stop member.

20. A trial implant according to claim 18, wherein the trial implant has a slot extending along at least one of the top or bottom thereof from front to back, and including a chisel cutting tool mountable on the trial implant for movement from back to front.

21. A device according to claim 20, including a set of a plurality of trial implants, which set comprises trial implants of the same height but having differing surface areas and having tail sections of differing lengths, such that for all of the trial implants of the set, the distance from the front of each trial implant to the rear of its tail section is the same, such that a given chisel fits all the trial implants of the set.

22. A device for preparing an intervertebral space, which device includes a trial implant to be inserted into an intervertebral space, an adjustable stop mechanism which includes a stop member located rearward of the trial implant and having a height great enough to engage a vertebrae as the trial implant moves into the intervertebral space, the adjustable stop mechanism being adjustable to change the distance between the back of the trial implant and the stop member to thereby change the insertion distance that the trial implant can move into the intervertebral space, the adjustable stop mechanism connected to the trial implant by a threaded engagement that allows relative movement between the trial implant and the stop member such that relative movement of the threaded engagement in one direction moves the stop member toward the trial implant and relative movement of the threaded engagement in the other direction moves the stop member away from the trial implant, the stop member mounted to freely rotate on a threaded member of the adjustable stop mechanism, and including an abutment surface of the trial implant which prevents the stop member from rotating about the axis of the threaded member, whereby, upon relative movement between the threaded member and the trial implant, by relative movement of the threaded engagement the stop member moves toward and away from the rear of the trial implant without rotating about the axis of the threaded member.

23. A device according to claim 22, including a bore extending through the trial implant, a portion of the bore being threaded and forming a part of said threaded engagement.

24. A device according to claim 23, the adjustable stop mechanism comprising an adjustment member which has the threaded portion thereon, wherein the stop member is mounted on the adjustment member so as to be freely rotatable thereon but restricted against longitudinal movement therealong.

25. A device according to claim 24, wherein the trial implant and the stop member engage each other to prevent rotation of the stop member and maintain it in a certain rotatable position wherein one or more arms of the stop member are in a vertical position so as to engage a vertebrae as the trial implant moves into the intervertebral space.

26. A device according to claim 22, including a shaft having a threaded end threadedly engaged in the trial implant, the adjustable stop mechanism being mounted on the shaft for free rotation therearound but restricted against movement longitudinally therealong.

27. A device for preparing an intervertebral space for reception of an implant, which device includes a trial implant which comprises a body portion of a shape adapted to fit into an intervertebral space, an adjustable stop mechanism which includes a stop member located rearwardly of the body portion and having a height great enough to engage a vertebrae as the body portion moves into the intervertebral space, the adjustable stop mechanism being adjustably engagable with the body portion and constructed to change the distance between the back of the body portion and the stop member to thereby change the insertion distance that the body portion of the trial implant can move into the intervertebral space, a threaded engagement connecting the adjustable stop mechanism to the body portion, wherein relative movement of the threaded engagement in one direction moves the stop member towards the body portion and relative movement of the threaded engagement in the other direction moves the stop member away from the body portion, and a bore formed into the back of the trial implant, the adjustable stop mechanism being moveable into and out of the bore to change the said insertion distance, the bore having a threaded portion which engages a threaded part of the adjustable stop mechanism.

28. A device according to claim 27, the adjustable stop mechanism comprising an adjustment member which has the threaded portion thereon, wherein the stop member is mounted on the adjustment member so as to be freely rotatable thereon but restricted against longitudinal movement therealong.

29. A device according to claim 28, wherein the body portion and the stop member engage each other to prevent rotation of the stop member and maintain it in a certain rotatable position wherein one or more arms of the stop member are in a vertical position so as to engage a vertebrae as the trial implant moves into the intervertebral space.

30. A device according to claim 29, wherein the body portion includes a slot adjacent the bore, and the stop member includes a projection which is received in the slot to prevent rotation of the stop member and maintain it in a proper rotative orientation with the arm or arms projecting vertically.

31. A device according to claim 28, wherein the adjustment member includes a structure at the rear end thereof to receive a tool to turn the adjustment member.

32. A device according to claim 28, wherein the adjustment member includes a central smooth shaft of lesser cross section than the threaded portion and an enlarged member spaced from the threaded portion, and the stop member including a sleeve rotatable on the smooth shaft between the threaded portion and the enlarged member and a pair of arms extending in opposite directions from the sleeve.

33. A device according to claim 32, wherein the body portion includes a slot adjacent the bore and the stop member includes a projection which is received in the slot to prevent rotation of the stop member and maintain a proper orientation of both of said arms projecting vertically.

34. A device for preparing an intervertebral space, including a shaft having a trial implant at the end thereof, which trial implant comprises a body portion of a shape adapted to fit into an intervertebral space, an adjustable stop mechanism which includes a stop member located rearwardly of the body portion and having a height great enough to engage a vertebrae as the body portion moves into the intervertebral space, the adjustable stop mechanism being adjustably engagable with the body portion and constructed to change the distance between the back of the body portion and the stop member to thereby change the insertion distance that the body portion of the trial implant can move into the intervertebral space, a threaded engagement connecting the adjustable stop mechanism to the body portion, wherein relative movement of the threaded engagement in one direction moves the stop member towards the body portion and relative movement of the threaded engagement in the other direction moves the stop member away from the body portion, said shaft having a threaded end threadedly engaged in the trial implant, the adjustable stop mechanism being mounted on the shaft for free rotation therearound but restricted against movement longitudinally therealong.

35. A device according to claim 34, the implant having a tail section narrower than the body portion, and the adjustable stop mechanism comprising a stop member which moves along the side of the tail section toward and away from the body portion.

36. A device according to claim 35, wherein the adjustable stop mechanism engages the side of the tail section to prevent rotation of the stop member.

37. A device according to claim 35, wherein the trial implant has a slot extending along at least one of the top or bottom thereof from front to back, and including a chisel cutting tool mountable on the trial implant for movement from back to front.

38. A device according to claim 37, including a set of a plurality of trial implants, which set comprises trial implants of the same height but having differing surface areas and having tail sections of differing lengths, such that for all of the trial implants of the set, the distance from the front of each trial implant to the rear of its tail section is the same, such that a given chisel fits all the trial implants of the set.

39. A device for preparing an intervertebral space, including a shaft having a trial implant at the end thereof, an adjustable stop mechanism which includes a stop member located rearward of the trial implant and having a height great enough to engage a vertebrae as the trial implant moves into the intervertebral space, the adjustable stop mechanism being adjustable to change the distance between the back of the trial implant and the stop member to thereby change the insertion distance that the trial implant can move into the intervertebral space, the adjustable stop mechanism connected to the trial implant by a threaded engagement that allows relative movement between the trial implant and the stop member such that relative movement of the threaded engagement in one direction moves the stop member toward the trial implant and relative movement of the threaded engagement in the other direction moves the stop member away from the trial implant, and the shaft having a threaded end threadedly engaged in the trial implant, the adjustable stop mechanism being mounted on the shaft for free rotation therearound but restricted against movement longitudinally therealong.

* * * * *